US011471072B2

(12) United States Patent
Lynde et al.

(10) Patent No.: US 11,471,072 B2
(45) Date of Patent: Oct. 18, 2022

(54) PULSE SENSOR, SYSTEM, AND METHOD FOR USING A PULSE SENSOR

(71) Applicant: INNOVAURA CORPORATION, Camano Island, WA (US)

(72) Inventors: C. Macgill Lynde, Bellevue, WA (US); Alan B. Corwin, Tacoma, WA (US); Ronald J. Schoenberg, Burien, WA (US); Keith Mullins, Kent, WA (US); David B. Goodson, Bellevue, WA (US); Derek Platt, Port Angeles, WA (US); Christopher A. Wiklof, Everett, WA (US)

(73) Assignee: INNOVAURA CORPORATION, Brier, WA (US)

( * ) Notice: Subject to any disclaimer, the term of this patent is extended or adjusted under 35 U.S.C. 154(b) by 0 days.

(21) Appl. No.: 17/206,065

(22) Filed: Mar. 18, 2021

(65) Prior Publication Data

US 2021/0275036 A1    Sep. 9, 2021

Related U.S. Application Data

(63) Continuation of application No. 17/032,342, filed on Sep. 25, 2020, now abandoned, which is a
(Continued)

(51) Int. Cl.
*A61B 5/11* (2006.01)
*A61B 5/00* (2006.01)
(Continued)

(52) U.S. Cl.
CPC .......... *A61B 5/1102* (2013.01); *A61B 5/0004* (2013.01); *A61B 5/024* (2013.01);
(Continued)

(58) Field of Classification Search
CPC ....... A61B 5/024; A61B 5/026; A61B 5/4875; A61B 5/681
See application file for complete search history.

(56) References Cited

U.S. PATENT DOCUMENTS 4,853,630 A     8/1989   Houston
5,069,221 A    12/1991   Smith et al.
(Continued)

OTHER PUBLICATIONS

International Preliminary Report on Patentability for International Application No. PCT/US2015/060209 dated May 16, 2017.
(Continued)

*Primary Examiner* — Oommen Jacob
(74) *Attorney, Agent, or Firm* — Launchpad Intellectual Property, Inc.; Christopher A. Wiklof

(57) ABSTRACT

A pulse sensor is capable of measuring a pulse rate of a wearer at a peripheral artery. In an embodiment, the pulse sensor includes a magnet supported to move responsive to an arterial pulse and a magnetometer configured to detect changes in a magnetic field produced by the magnet. The magnet may include a plurality of ferromagnetic particles disposed in or on a flexible substrate configured to be held adjacent to human skin subject to arterial palpation and a magnetic sensor configured to sense movement of the ferromagnetic particles. A system and method may measure hydration includes using a pulse sensor to measure pulse rate and modulation. The wearer is prompted when the pulse rate and pulse modulation indicate a response to dehydration of the wearer.

10 Claims, 14 Drawing Sheets

Related U.S. Application Data continuation-in-part of application No. 15/591,918, filed on May 10, 2017, now Pat. No. 10,791,964, which is a continuation of application No. PCT/US2015/060209, filed on Nov. 11, 2015.

(60) Provisional application No. 62/078,012, filed on Nov. 11, 2014, provisional application No. 62/078,387, filed on Nov. 11, 2014.

(51) Int. Cl.

| | | |
|---|---|---|
| A61B 5/05 | (2021.01) | |
| A61B 5/024 | (2006.01) | |
| A61B 5/242 | (2021.01) | |
| A61B 5/243 | (2021.01) | |
| A61B 5/026 | (2006.01) | |
| A61B 5/0255 | (2006.01) | |

(52) U.S. Cl.
CPC ........... *A61B 5/026* (2013.01); *A61B 5/0255* (2013.01); *A61B 5/02438* (2013.01); *A61B 5/05* (2013.01); *A61B 5/11* (2013.01); *A61B 5/1126* (2013.01); *A61B 5/242* (2021.01); *A61B 5/243* (2021.01); *A61B 5/4875* (2013.01); *A61B 5/681* (2013.01); *A61B 5/6824* (2013.01); *A61B 5/725* (2013.01); *A61B 5/7221* (2013.01); *A61B 5/7257* (2013.01); *A61B 5/7278* (2013.01); *A61B 5/742* (2013.01); *A61B 5/746* (2013.01); *A61B 5/7475* (2013.01); *A61B 5/4866* (2013.01); *A61B 2560/0214* (2013.01); *A61B 2562/0219* (2013.01); *A61B 2562/0223* (2013.01); *A61B 2562/164* (2013.01); *A61B 2562/18* (2013.01)

(56) References Cited

U.S. PATENT DOCUMENTS

| | | | |
|---|---|---|---|
| 5,913,826 A * | 6/1999 | Blank | A61B 5/412 600/500 |
| 7,391,210 B2 | 6/2008 | Zhang et al. | |
| 7,485,094 B2 * | 2/2009 | Marks | A61B 5/0535 600/500 |
| 7,824,340 B2 * | 11/2010 | Lee | A61B 5/6844 600/500 |
| 8,094,009 B2 * | 1/2012 | Allen | A61B 5/02007 340/539.12 |
| 8,394,067 B2 | 3/2013 | Bracken et al. | |
| 8,923,941 B2 | 12/2014 | LeBoeuf et al. | |
| 9,770,600 B1 | 9/2017 | Demas et al. | |
| 10,980,491 B1 * | 4/2021 | Jones | A61B 5/746 |
| 2001/0026222 A1 | 10/2001 | Canady, Jr. et al. | |
| 2003/0144705 A1 | 7/2003 | Funke | |
| 2003/0212335 A1 | 11/2003 | Huang | |
| 2004/0061620 A1 | 4/2004 | Devine | |
| 2005/0274454 A1 | 12/2005 | Extrand | |
| 2006/0122484 A1 | 6/2006 | Itozaki et al. | |
| 2006/0206031 A1 | 9/2006 | Hasagawa | |
| 2006/0229809 A1 | 10/2006 | Chen | |
| 2007/0118040 A1 | 5/2007 | Lee et al. | |
| 2007/0179386 A1 | 8/2007 | Michard et al. | |
| 2008/0047154 A1 | 2/2008 | Steinich | |
| 2008/0097230 A1 | 4/2008 | Marks et al. | |
| 2008/0294019 A1 * | 11/2008 | Tran | A61B 5/4875 600/301 |
| 2011/0054270 A1 | 3/2011 | Derchak | |
| 2011/0245711 A1 * | 10/2011 | Katra | A61B 5/1072 600/547 |
| 2012/0143019 A1 * | 6/2012 | Russell | A61B 5/7271 600/301 |
| 2012/0197093 A1 | 8/2012 | LeBoeuf et al. | |
| 2013/0099735 A1 | 4/2013 | Partovi | |
| 2013/0165766 A1 | 6/2013 | Nishikawa et al. | |
| 2014/0228649 A1 | 8/2014 | Rayner et al. | |
| 2014/0243617 A1 | 8/2014 | LeBoeuf et al. | |
| 2014/0275854 A1 | 9/2014 | Venkatraman et al. | |
| 2014/0288391 A1 | 9/2014 | Hong et al. | |
| 2014/0316287 A1 * | 10/2014 | Watson | A61B 5/742 600/485 |
| 2014/0371886 A1 * | 12/2014 | Jain | G16H 40/67 700/91 |
| 2015/0057511 A1 | 2/2015 | Basu | |
| 2015/0105630 A1 | 4/2015 | Kummerl et al. | |
| 2015/0182160 A1 | 7/2015 | Kim et al. | |
| 2015/0196251 A1 * | 7/2015 | Outwater | A61B 5/14551 600/301 |
| 2016/0007925 A1 | 1/2016 | Mirov et al. | |
| 2016/0058389 A1 * | 3/2016 | Lee | A61B 5/02055 600/301 |
| 2016/0213560 A1 | 7/2016 | Sturdivant | |
| 2016/0262687 A1 | 9/2016 | Vaidyanathan et al. | |
| 2016/0317089 A1 * | 11/2016 | Fyfe | A61B 5/7282 |
| 2016/0327915 A1 | 11/2016 | Katzer et al. | |
| 2017/0249445 A1 * | 8/2017 | Devries | G16H 20/60 |
| 2017/0258410 A1 | 9/2017 | Gras | |
| 2017/0311849 A1 | 11/2017 | Lynde et al. | |
| 2018/0085057 A1 | 3/2018 | Lynde et al. | |
| 2021/0275036 A1 * | 9/2021 | Lynde | A61B 5/024 |

OTHER PUBLICATIONS

Kaniusas et al., "Method for Continuous Nondisturbing Monitoring of Blood Pressure by Magnetoelastic Skin Curvature Sensor and ECG", IEEE Sensors Journal, vol. 6, No. 3, Jun. 2006, pp. 819-828.

Huang et al., "Epidermal Differential Impedance Sensor for Conformal Skin Hydration Monitoring", Biointerphases, 7:52, Published on-line Aug. 23, 2012, 9 pages.

* cited by examiner

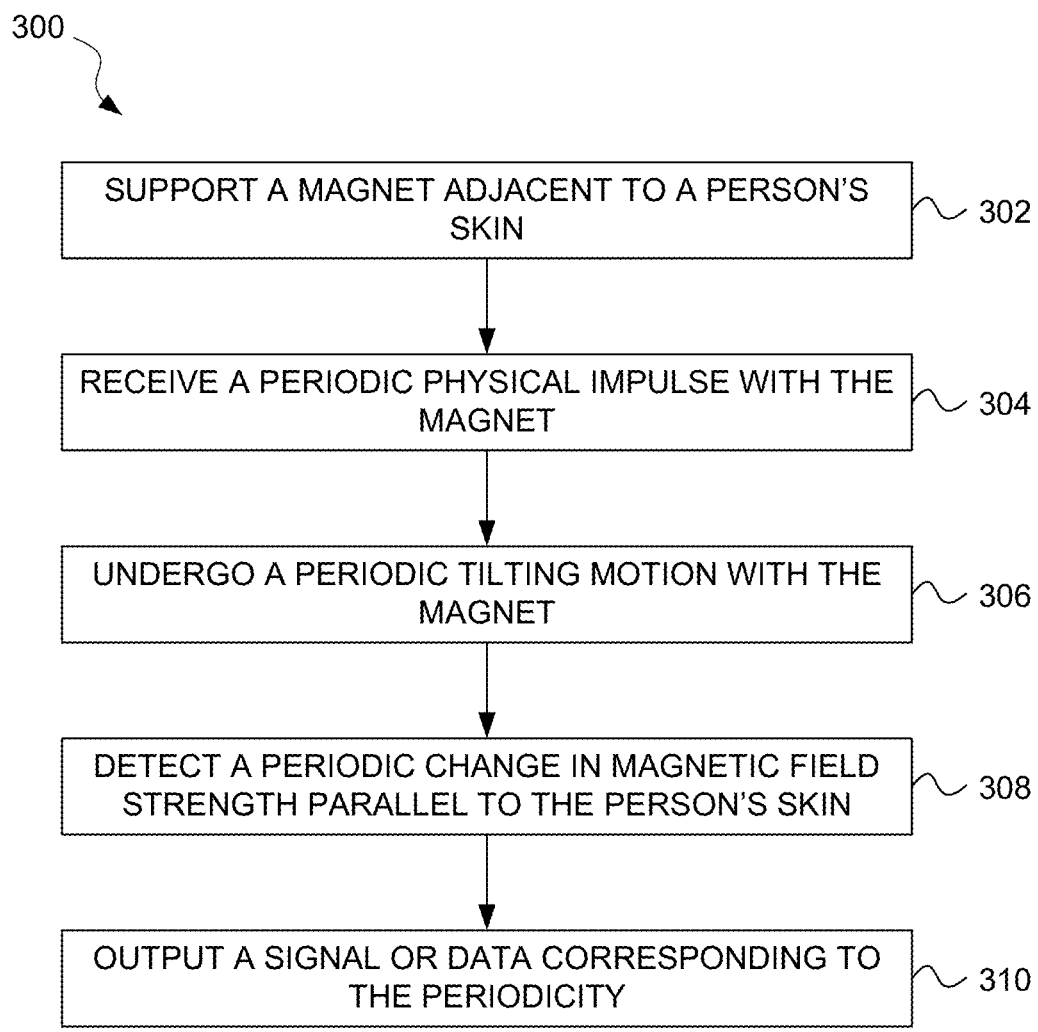

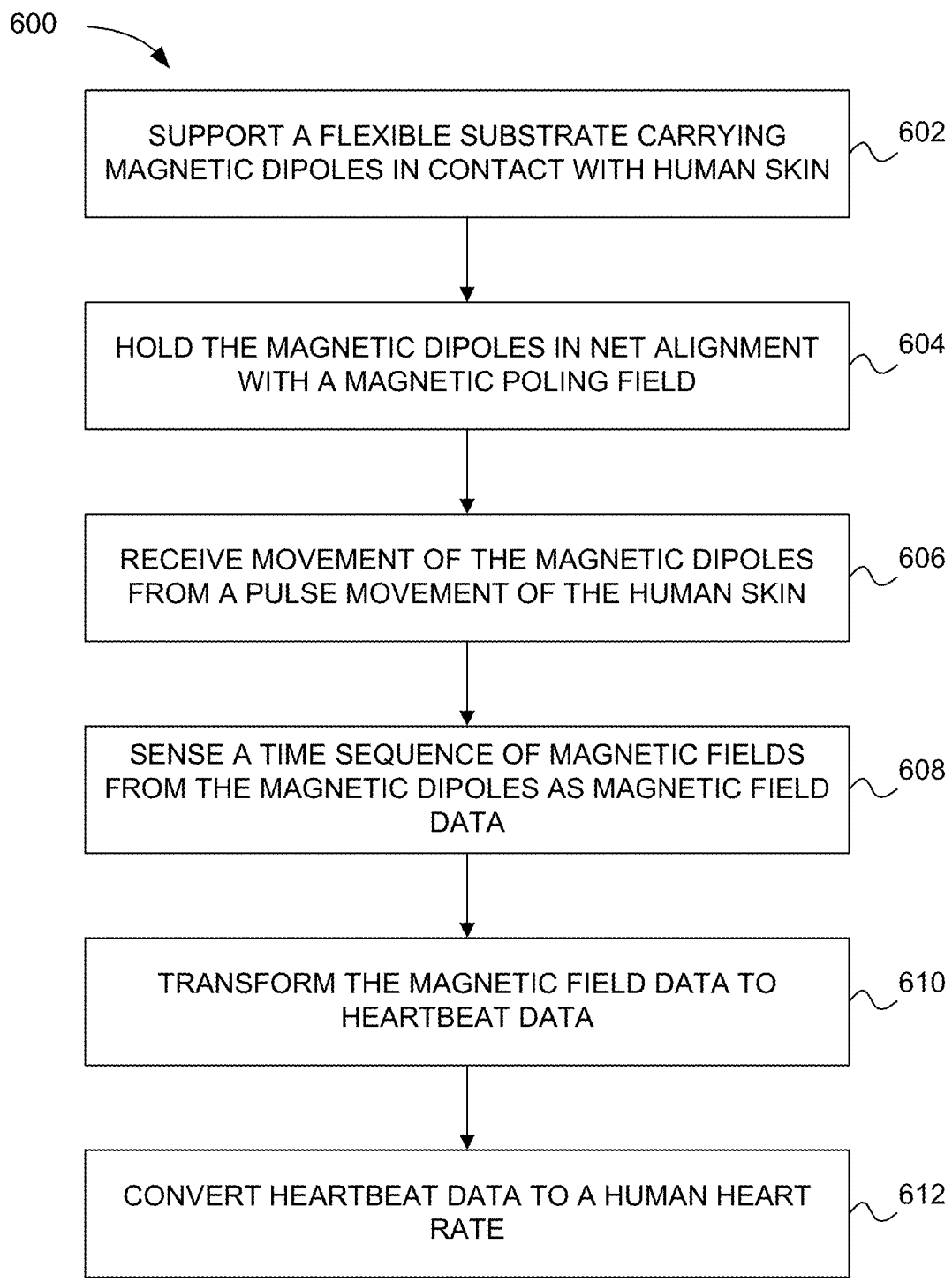

PULSE SENSOR, SYSTEM, AND METHOD FOR USING A PULSE SENSOR

SUMMARY

According to an embodiment, a pulse monitor includes a sensor disposed over an artery (e.g., a peripheral artery), such as a wrist-worn sensor that may detect a periodic expansion of the radial artery. The frequency of the periodic expansion is indicative of heart rate. In an embodiment, a magnitude of periodic expansion is indicative of blood volume. According to embodiments, the detected heart rate and blood volume are correlated to infer a state of hydration of the wearer. According to an embodiment, the detected heart rate and blood volume are correlated to infer a rate of caloric output.

During normal changes in hydration, human blood volume changes. Serum volume is decreased as overall hydration decreases. This may be exhibited as an overall increase in blood viscosity. Blood is a (shear-thinning) non-Newtonian fluid that is characterized by relatively high viscosity during low-shear conditions and relatively low viscosity during high-shear conditions. The systolic phase of pulse tends to be characterized by higher shear force on the blood compared to the diastolic phase. Due to blood's response to shear force, the viscosity is higher during the diastolic phase than during the systolic phase.

During exercise, moderate dehydration may be accompanied by an increase in peripheral blood pressure (BP), with diastolic BP increasing somewhat more than systolic BP, and by an increase in pulse rate. During severe dehydration, peripheral BP may decrease as the body redirects blood flow to vital organs.

A human pulse wave is characterized by a peak resulting from the heart's contraction during systole, quickly followed by a smaller hump (also referred to as a peak herein) resulting from wave reflection during diastole. The inventors have discovered that the change in systolic wave peak-to-reflected wave peak, as measured by the differential peripheral artery expansion, changes as a function of blood viscosity and may be used to estimate hydration even without a blood pressure cuff or other apparatus for measurement of absolute (or gauge) blood pressure. In an embodiment, changes in differential peripheral artery expansion may be combined with changes in pulse rate to further refine the estimate of hydration. The inventors contemplate that detected arterial expansion and heart rate may be used to infer caloric output. The inventors further contemplate detecting differential peripheral artery expansion to estimate or infer other medical, health, and/or nutritional conditions.

According to an embodiment, an increase in blood viscosity results in decreased differential expansion of peripheral arteries, with a corresponding decrease in signal modulation generated responsive to the differential expansion. The body may compensate by simultaneously increasing heart rate. In an embodiment, the health monitor sensor includes a pulse sensor that simultaneously measures heart rate and systolic peak to diastolic hump arterial expansion ratio, which is expressed as modulation. A mobile pulse sensor application may correlate the heart rate and modulation, estimate a hydration state of a user, and drive a user interface to alert the user to drink fluids in order to maintain optimal hydration.

Optionally, the pulse sensor may be configured to simultaneously measure athletic exertion. For example, the pulse sensor may measure apparent motion of far field magnetic field (e.g., earth's magnetic field) or otherwise sense accelerations corresponding to gross motor movements of a person. The pulse monitor application may correlate the measurements to provide enhanced sensitivity and improved rejection of spurious measurements.

Optionally, the pulse sensor may include a skin impedance sensor. Detected skin impedance combined with detected blood volume may provide data to inform a process for estimating hydration.

According to embodiments, a hydration estimation process may be performed with a programmable or application specific logic device (such as an FPGA or ASIC) or as a computational thread supported by a microcontroller or microprocessor. In an embodiment, the process may be disposed at least partly on a networked server operatively coupled to the local pulse sensor hardware.

According to an embodiment, a method for monitoring the hydration of a person includes measuring a physical periodic motion corresponding to a peripheral artery with a pulse sensor to determine pulse data, each measured physical periodic motion corresponding to a sequence of instantaneous arterial size estimates or derivatives thereof. The method includes outputting the pulse data (which pulse data may include a modulation and a pulse rate) and receiving one or more instances of pulse data with a programmable hardware device (such as a microcontroller). The method may include saving the modulation and pulse rate to a buffer memory as a modulation history and pulse rate history. The method may include calculating a combined modulation and pulse rate limit from the modulation and pulse rate history. The method may include writing the pulse data to a memory device as an instant in an arterial pulsation history, and reading the arterial pulsation history. The method may include determining, with a microcontroller, at least one limit including at least one of a pulse wave modulation value, a pulse rate value, and a blood flow value from the arterial pulsation history. The method may include writing the at least one limit to a non-transitory computer readable medium, receiving one or more new pulse data sets, calculating at least one new variable value from the one or more new pulse data sets, and comparing, with the programmable hardware device, the at least one new variable value to the at least one limit. The microcontroller outputs a prompt via a user interface to the person if a predetermined number of instances of the at least one new variable value falls outside the at least one limit, indicating a probable need for rehydration. Optionally, the modulation and/or pulse rate limit may be expressed as a derivative, such that the method looks for changes in slope of modulation and/or pulse rate vs. time.

According to an embodiment, a non-transitory computer readable medium carrying computer executable instructions configured to cause a portable device to execute a method includes the steps of measuring a physical periodic motion of a peripheral artery with a pulse sensor, each measured physical periodic motion including a modulation and a pulse rate; receiving the modulation and pulse rate with a microcontroller; and saving the modulation and pulse rate to a buffer memory as a modulation history and pulse rate history. The microcontroller may determine a modulation, estimated instantaneous blood flow rate, and pulse rate limit from the modulation and pulse rate history. The modulation, blood flow rate and pulse rate limit may be written to a non-transitory computer readable medium. The microcontroller compares one or more measured instances of the modulation, blood flow rate and corresponding pulse rate to the modulation, blood flow rate and pulse rate limit. The microcontroller outputs, via a user interface, a prompt to the person if the one or more measured instances of the modulation, blood flow rate and pulse rate falls outside the modulation, blood flow rate and pulse rate limit.

The method for monitoring a human pulse may include using one or more magnetic sensor(s) to measure the change in magnetic flux arising from the perturbation of a magnetic field where such field is created by magnets or magnetic particles positioned on the wrist at the radial artery.

According to an embodiment, a method may extend the functionality of the apparatus to monitor relative blood flow and, along with other inputs, allows an estimate of relative state of hydration. Blood flows through arteries as waves created by the pumping action of the heart. The change in magnetic flux is proportional to the change in the radius of the artery created by the pulse wave. The method may include calculating positive changes in arterial radius during a pulse wave by a formula relating change in magnetic flux to change in radius. The formula may be derived empirically and depends on location of sensors relative to magnetic field, among other factors. The method may also include sampling the magnetic flux frequently in order to sum the radius measurements to calculate an estimate of the volume of the portion of the wave that is distending the artery during systolic and diastolic phases and calculating an index of blood flow as a function of the above wave volume multiplied by the frequency of waves (i.e. pulse rate).

Changes in hydration may result in changes in modulation, pulse and blood flow, but these changes may also be moderated by changes in exercise and body temperature.

The pulse sensor may include a temperature sensor to measure skin temperature as an index of body temperature and accelerometer or accelerometer/gyro to monitor motion as an index of exercise. An index of hydration may be calculated as a function using the modulation, blood flow index, pulse rate, optionally body temperature index and optionally exercise index.

According to an embodiment, a method includes generating, with a pulse sensor positioned adjacent to a peripheral artery of a person, pulse sensor signals indicative of movement of the peripheral artery, calculating, with a digital processor, a pulse rate and a modulation of the peripheral artery based on the pulse sensor signals, and comparing, with the digital processor, the pulse rate and the modulation to reference pulse rates and reference modulations. The method includes determining, with the digital processor, a state of hydration of the person based on the comparison of the pulse rate and modulation to the reference pulse rates and reference modulations, and outputting an alert to the user if the state of hydration corresponds to the person being dehydrated.

According to an embodiment, a pulse sensor includes at least one magnet disposed adjacent to a user's artery subject to pulse movement, the magnet being subject to movement responsive to the arterial pulse movement. A magnetometer is configured to measure a magnetic field produced by the at least one magnet and to measure variations in the magnetic field corresponding to the movement of the magnet responsive to the arterial pulse movement. A sensing circuit is operatively coupled to the magnetometer and configured to infer a heart rate corresponding to the sensed variations in the magnetic field.

According to an embodiment, a pulse sensor includes a flexible membrane configured to be held adjacent to a user's skin at a location corresponding to an artery subject to pulse movement and at least one magnet having a magnetic axis, the magnet being disposed on the flexible membrane and being configured to physically tilt responsive to the pulse movement, whereby the magnetic axis tilts. A magnetometer is configured to measure a magnetic field produced by the at least one magnet, the magnetometer having a magnetic field measurement axis along which the magnetic axis tilt causes a change in measured magnetic field strength.

According to another embodiment, a pulse sensor includes a flexible membrane configured to be held adjacent to a user's skin at a location corresponding to an artery subject to pulse movement, at least one magnet disposed on the flexible membrane and configured to move responsive to the pulse movement, and a magnetometer configured to measure variations in a magnetic field from the at least one magnet responsive to the pulse movement. A motion sensor may be configured to detect movement of the human. A microcontroller operatively coupled to the magnetometer and the motion sensor may include a non-transitory computer-readable medium carrying microcontroller instructions configured to cause the microcontroller to receive data or a signal from the magnetometer, receive detected movement information from the motion sensor, filter the data or signal from the first magnetometer responsive to the detected movement, and output heart rate data corresponding to the filtered data or signal from the first magnetometer.

According to embodiments, the motion sensor may also provide user motion data to fitness and health tracking applications, devices, and/or systems. In a particular embodiment, a sensor device outputs motion data and heart rate data to a fitness or health tracking application. The fitness or health tracking application is embodied as a non-transitory computer readable medium carrying computer instructions that cause the application to correlate a sequence of motion data to a corresponding sequence of heart rate data. The application may perform logical operations, for example using Bayesian logic, on the correlated data to determine a probability of a user having a fitness corresponding to any of a plurality of levels; and display the most probable fitness level to the user.

According to an embodiment, a method for detecting a heart rate includes supporting a magnet adjacent to the skin of a person, receiving a periodic physical impulse with the magnet responsive to arterial movement during systole and diastole, and undergoing a periodic tilting motion of the magnet responsive to the periodic physical impulse corresponding to systole and diastole. A magnetometer detects a periodic change in the strength of the magnetic field produced by the magnet along an axis parallel to the person's skin and outputs a magnetometer signal or magnetometer data corresponding to a periodicity of the detected periodic change in the strength of the magnetic field. The output signal or data includes a component corresponding to a heart rate of the person.

According to an embodiment, a method for tracking the heart rate of a person includes flexibly supporting a magnet adjacent to a pulse detection location of a person, undergoing, with the magnet, movement responsive to pulse movement of the person, and operating a magnetometer to detect periodic changes in magnetic field strength from the magnet, the periodic changes in magnetic field strength corresponding to the movement of the magnet and the pulse movement of the person. A microcontroller receives magnetometer data including the periodic changes in magnetic field strength from the magnet and transforms the magnetometer data to produce frequency data. The microcontroller receives motion data corresponding to movement of the person from a motion detector. The microcontroller uses the motion data to filter the frequency data to select a frequency most likely to correspond to a pulse rate of the person.

According to an embodiment, a pulse sensor includes a flexible substrate configured for support against a human skin surface, a plurality of aligned magnetic dipoles supported by the flexible substrate, a magnetic sensor configured to detect magnetic fields emitted by the plurality of magnetic dipoles, and an analysis circuit operatively coupled to the magnetic sensor. According to an embodiment, the flexible substrate may include a gel material. The magnetic dipoles may be suspended in the gel. In an embodiment, the magnetic dipoles may be formed from magnetic nano-beads, or alternatively from crushed or otherwise finely divided portions of a poled permanent magnet. In an embodiment, high coercivity magnetic dipoles may be magnetically aligned during manufacture and locked into alignment by cross-linking or otherwise fixing relative alignment of the magnetic dipoles. In another embodiment, high coercivity magnetic dipoles may be held in alignment during use by a magnet configured to pass a magnetic field through the magnetic dipoles.

In another embodiment, the magnetic dipoles may be formed from a low coercivity material. The low coercivity particles may be induced to be aligned magnetic dipoles by a magnet configured to pass a magnetic field through the low coercivity particles.

According to an embodiment, a method for detecting a human pulse includes supporting a flexible substrate carrying aligned magnetic dipoles against a human skin surface subject to motion caused by a human pulse, sensing a time sequence of magnetic field data including a component corresponding to the aligned magnetic dipoles subject to motion caused by the human pulse, and transforming the magnetic field data to heartbeat data corresponding to the sensed human pulse.

According to an embodiment, the method may include mechanically maintaining alignment of the magnetic dipoles. According to another embodiment, the method may include applying a magnetic field to the magnetic dipoles to hold the magnetic dipoles in alignment. According to another embodiment, the magnetic dipoles may be formed as low coercivity particles, and the method may include applying a magnetic field to the low coercivity particles to cause the low coercivity particles to be magnetized in alignment with the magnetic field, thereby becoming aligned magnetic dipoles.

BRIEF DESCRIPTION OF THE DRAWINGS

Non-limiting embodiments of the present disclosure are described by way of example with reference to the accompanying figures, which are schematic and are not intended to be drawn to scale. Unless indicated as representing the background art, the figures represent aspects of the disclosure.

FIG. 3 is a flow chart of a method for detecting a heart rate, according to an embodiment.

FIG. 6 is a flowchart showing a method for detecting a human pulse, according to an embodiment.

DETAILED DESCRIPTION

Figure 1:
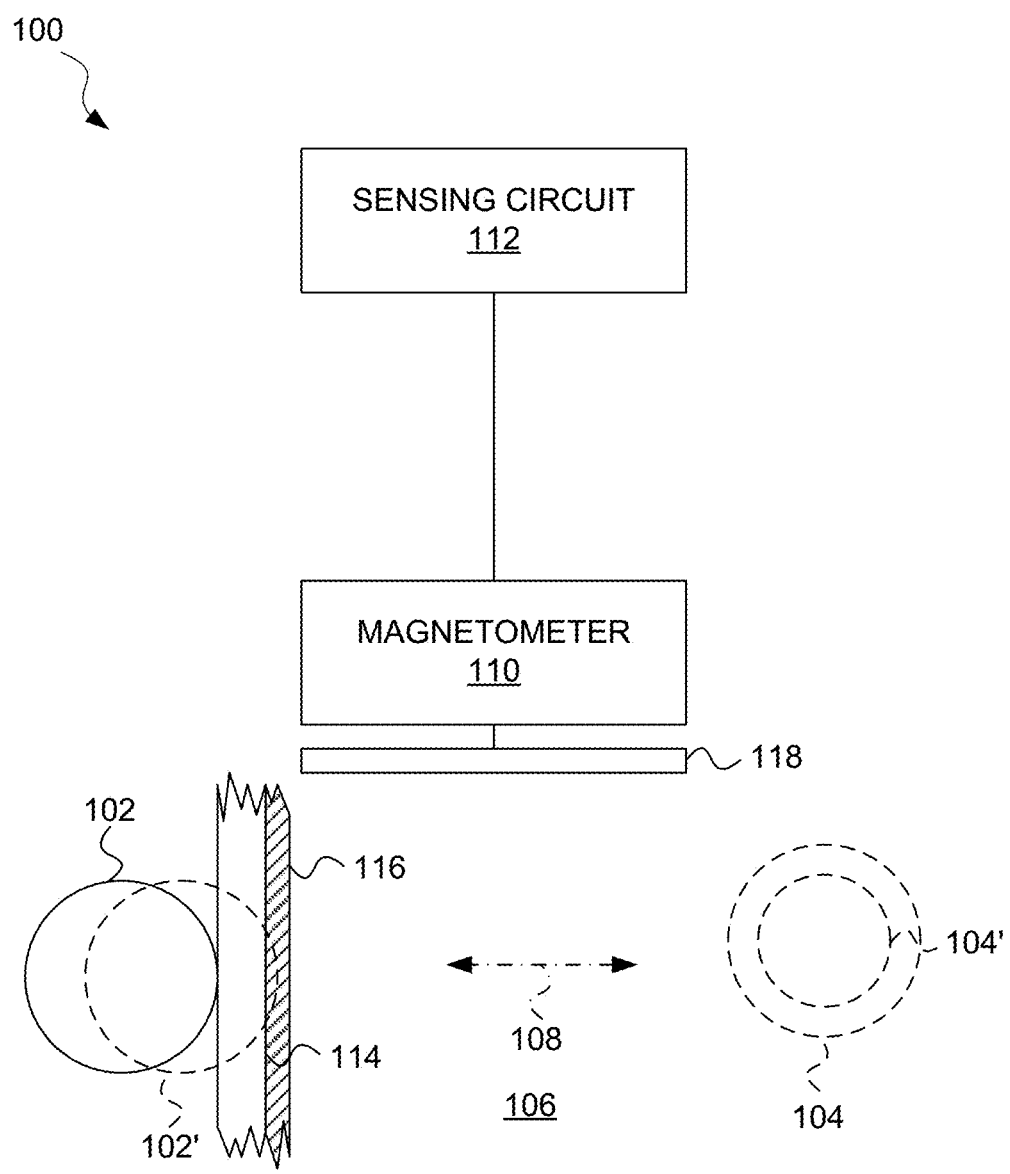
FIG. 1 is a diagram of a pulse sensor, according to an embodiment.

In the following detailed description, reference is made to the accompanying drawings, which form a part hereof. In the drawings, which are not to scale or to proportion, similar symbols typically identify similar components, unless context dictates otherwise. The illustrative embodiments described in the detailed description, drawings and claims, are not meant to be limiting. Other embodiments may be used and/or other changes may be made without departing from the spirit or scope of the present disclosure.

The terms heart rate and pulse rate are used interchangeably herein. As used herein, the term pulse sensor refers to a device capable of measuring a pulse of a wearer. A heart rate monitor is a type of pulse sensor that measures pulse rate. A health monitor includes a pulse sensor that measures aspects of a pulse, including pulse rate, that may be used to infer a physical condition of a wearer. According to embodiments, a pulse sensor may also be considered a health monitor when the pulse sensor is capable of measuring a variable corresponding to relative pressure or dilation during systolic and diastolic portions of a pulse.

For purposes of clarity, the term pulse monitor is used as a generalization of the terms heart rate monitor and health monitor, wherein specificity may be inferred by recited function and may optionally be directly specified by incorporations by reference of patents and applications from which this application draws priority.

FIG. 1 is a diagram of a pulse sensor 100, according to an embodiment. The pulse sensor 100 includes at least one magnet 102 disposed adjacent to a user's artery 104 subject to pulse movement, the magnet 102 being subject to movement responsive to the arterial pulse movement. The user's tissue 106 provides compressive and tensile strength 108, and itself conveys motion responsive to the arterial pulsations 104, 104'. The tissue 106 thus conveys motion between locations 102, 102' occupied by the magnet 102. The orientation of the poles of the magnet(s) 102 may be oriented according to various axes as described in respective embodiments below.

A magnetometer 110 is positioned within and configured to measure a magnetic field produced by the at least one magnet 102 and is configured to measure variations in the magnetic field corresponding to the movement of the magnet responsive to the arterial pulse movement. A sensing circuit 112 is operatively coupled to the magnetometer 110 and configured to infer a heart rate corresponding to the sensed variations in the magnetic field. For example, the sensing circuit 112 may be physically coupled to the magnetometer 110.

Alternatively, at least a portion of the sensing circuit 112 may be operatively coupled to the magnetometer 110 via a radio interface. For example, the pulse sensor 100 may include a first radio communication circuit configured to output data corresponding to a signal from the magnetometer 110 via a radio signal, a second radio communication circuit configured to receive the data from the first radio communication circuit via the radio signal, and a data logging circuit operatively coupled to the second radio communication circuit. In this arrangement, for example, a portion of the sensing circuit 112 including an analog-to-digital converter may receive analog input from the magnetometer 110, and convert the analog signal to a digital value that is then output via the first and second radio circuits to another portion of the sensing circuit 112.

In an embodiment, a flexible membrane 114 may be configured to be held adjacent to the user's skin at a location corresponding to the artery 104 subject to pulse movement and the at least one magnet 102 may be disposed on the flexible membrane 114. Optionally, a pressure sensitive adhesive coating 116 may be disposed on the flexible membrane 114 to hold the flexible membrane 114 adjacent to the user's skin. In another embodiment, a housing 118 may be configured to support the flexible membrane 114 against the user's skin. In another embodiment, the at least one magnet 102 is subcutaneously embedded within the user's tissue 106 at a location near the artery 104.

Figure 2A:
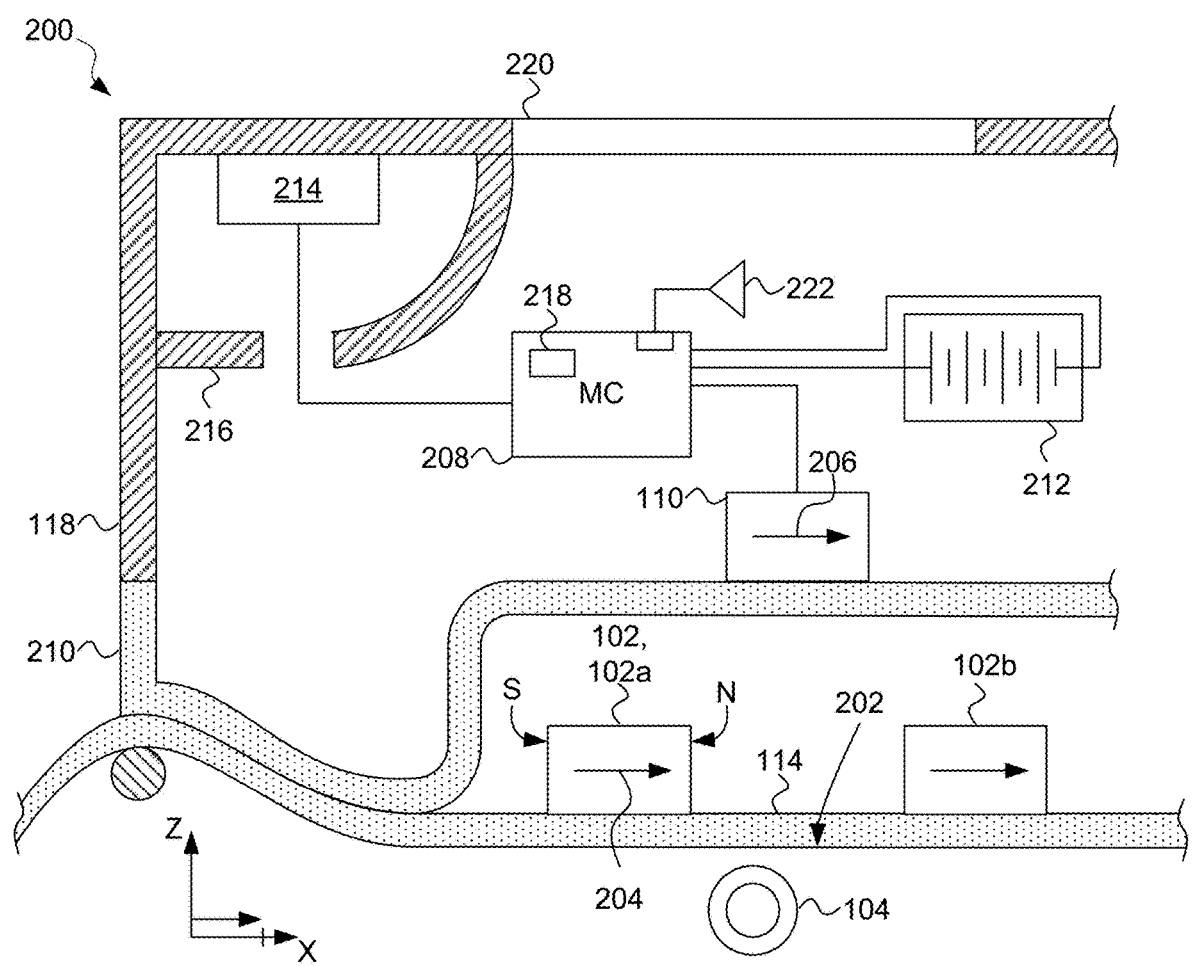
FIG. 2A is a diagram of a pulse sensor during a diastolic portion of a user's heartbeat, according to an embodiment.
Figure 2B:
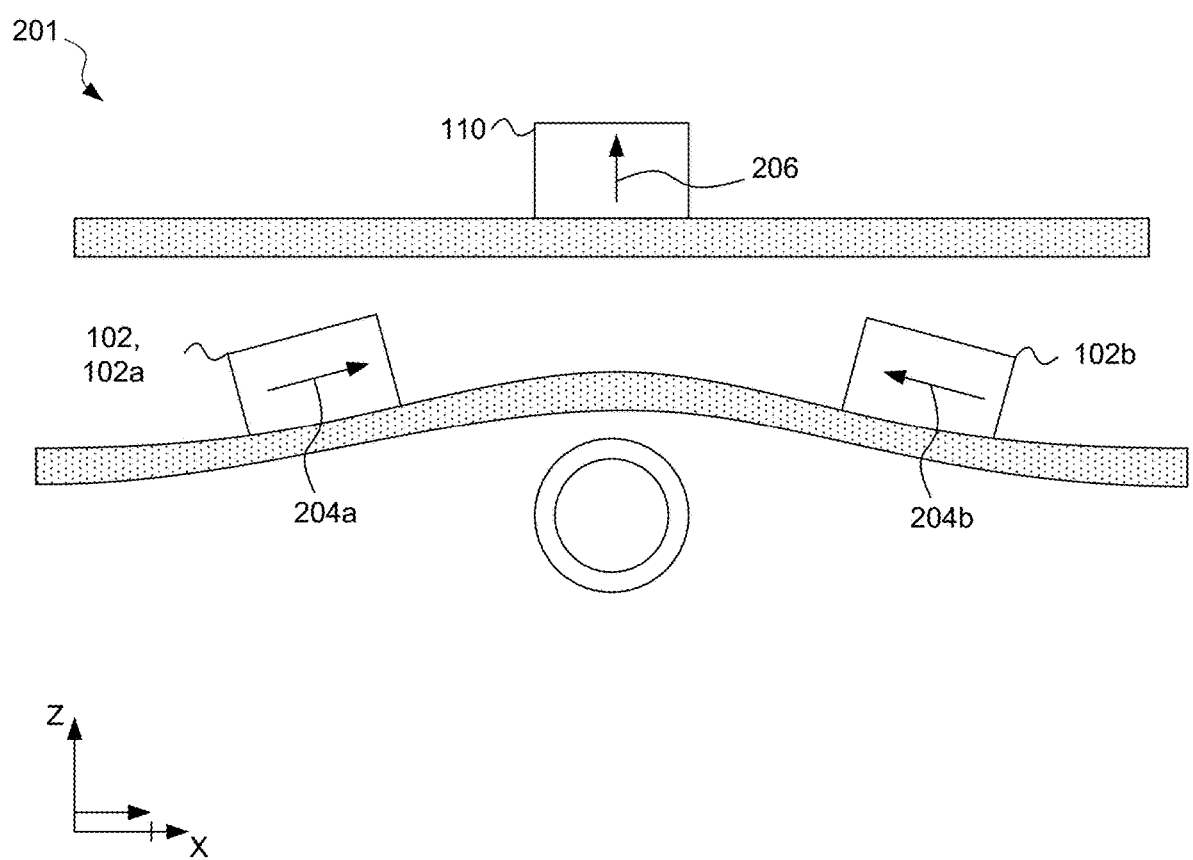
FIG. 2B is a diagram of a portion of the pulse sensor of FIG. 2A during a palpated portion of the user's heartbeat and including an alternative magnetic field design, according to an embodiment.

FIG. 2A is a diagram of a pulse sensor 200 during a diastolic portion of a user's heartbeat, according to an embodiment. FIG. 2B is a diagram 201 of a portion of the pulse sensor 200 of FIG. 2A during a palpated portion of the user's heartbeat and including an alternative magnetic field design, according to an embodiment. Referring to FIGS. 2A and 2B, the pulse sensor 200 may include a flexible membrane 114 configured to be held adjacent to a user's skin 202 at a location corresponding to an artery 104 subject to pulse movement. At least one magnet 102 having a magnetic axis 204 is disposed on the flexible membrane 114. By supporting the flexible membrane 114 and the at least one magnet 102 against the user's skin 202 over the artery 104, the at least one magnet 102 may be configured to physically tilt responsive to the pulse movement, whereby the magnetic axis 204 tilts. FIG. 2A shows a diastolic portion of the heartbeat when the artery 104 is contracted. The magnet(s) 102 tend to lie in plane with the user's skin 202. FIG. 2B shows a palpated portion of the heartbeat when the artery 104 expands under systolic pumping pressure from the heart. As may be seen, the magnet(s) 102 and corresponding magnetic axis 204 (axes) is (are) tilted up responsive to the pulse movement.

As used herein, the term magnetic axis 204 is defined relative to a magnet 102; that includes a north pole (indicated as N) and a south pole (indicated as S); such that the magnetic axis 204 is a line intersecting both the north pole and the south pole of the magnet 102.

The magnetometer 110 is configured to measure a magnetic field produced by the at least one magnet 102, the magnetometer 110 having a magnetic field measurement axis 206 along which the magnetic axis 204 tilt causes a change in measured magnetic field strength. The detected magnetic field strength varies according to the tilt angle of the magnetic axis 204 relative to the measurement axis 206. A periodicity corresponding to the detected magnetic field strength corresponds to the systolic-diastolic rhythm, and thus serves as a measurement of heart rate.

Moreover, it may be appreciated that the difference between magnet(s) angles, expressed as a difference in maximum and minimum detected magnetic field strength, may be proportional to a difference between systolic and diastolic blood pressure, which can, it is contemplated, be related to gauge blood pressure of the user.

The arrangement depicted in FIGS. 2A and 2B may be especially useful for cases where the magnetometer 110 either does not have the ability to measure changes in magnetic field strength in the z-axis normal to the skin 202 of the user; or where the signal to noise ratio, sensitivity, or accuracy of z-axis measurement is inferior to measurements taken along the x-axis, which is nominally parallel to the magnetic axis (axes) 204 of the magnet(s) 102. This aspect may be leveraged to minimize or reduce z-axis height of the magnetometer 110 and/or to minimize or reduce z-axis height of the housing 118 (such as a portion of a smart watch band) that forms a portion of the pulse sensor 200.

In some embodiments, the magnetic field measurement axis 206 may be selected to be momentarily parallel to the plane of the magnetic axis 204 of the at least one magnet 102 during a pulse period. This may occur once per period if the magnetic axis 204 is parallel to the measurement axis 206 either at diastole or at systole; or it may occur twice per period if the magnetic axis 204 is momentarily parallel to the magnetic field measurement axis 206 at a point other than maximum or minimum angular displacement (e.g., at a point in the period other than diastole or systole). In other embodiments (e.g., if the magnet 102 is at a different angular position along a curved skin surface from the magnetometer 110), the magnetic axis 204 is never parallel to the magnetic field measurement axis 206 during heart rate measurement. Nevertheless, the measured magnetic field strength along the magnetic field measurement axis 206 will vary during the pulse period if the magnet(s) 102 is supported sufficiently close to the artery 104 that the magnet 102 tilts responsive to pulse.

As illustrated in FIGS. 2A, 2B, and 3, the at least one magnet 102 may include a plurality of magnets 102a, 102b disposed to cause at least two of the plurality of magnets 102a, 102b to physically tilt responsive to the pulse movement of the artery 104 and the skin 202. In some embodiments, there may be precisely two magnets 102a, 102b that are configured to align with the pulse point when the user dons the apparatus 200. In other embodiments, there may be three, four, or a large plurality of magnets 102a, 102b located along the flexible membrane 114, such that a gap between two of the magnets 102a, 102b will span the pulse measurement position over the artery 104. This may be used, for example, to improve tolerance for rotational displacement of the apparatus 200 around the user's wrist, improve tolerance to physical morphology differences between users, and/or allow for a loser fit of the flexible membrane 114.

Referring especially to FIG. 2A, the pulse sensor 200 may include a microcontroller 208 operatively coupled to the magnetometer 110. The housing 118 may be configured to support the magnetometer 110 and configured to urge the flexible membrane 114 against the user's skin 202. The housing 118 may include a magnetically transparent housing portion 210 selected to pass the magnetic field produced by the magnet(s) 102 to the magnetometer 110. For example, the magnetically transparent housing portion 210 may be formed from a non-ferromagnetic material such as a plastic or aluminum. Additionally or alternatively, the housing 118 may be configured to support the magnetometer 110 between the housing 118 and the magnet 102 (configuration not shown). In this configuration, it may still be preferable for the housing 118 to be non-ferromagnetic in order to avoid distorting magnetic field lines from the magnet(s) 102.

The pulse sensor 200 may further include a battery 212 contained within the housing 118 and configured to provide sufficient power to maintain function of the pulse sensor 200 for at least 24 hours. In some embodiments, the microcontroller 208 may go to sleep and receive motion and/or heart rate data responsive to a predetermined interval. When motion and/or heart rate is relatively constant or has a low value, the microcontroller 208 may be programmed to go back to sleep. When motion and/or heart rate data has changed since a previous sample, the microcontroller 208 may be programmed to wake up and track heart rate and motion, and output data corresponding to heart rate and motion. When motion decreases and heart rate drops, the microcontroller 208 may be programmed to go back to sleep. The combination of a low power microcontroller and the inherently low power consumption of the magnetometer 110 used for heart rate detection may enable the battery 212 to provide sufficient power to maintain function of the pulse sensor 200 for at least one week. This is possible with current battery technology owing to the very low power consumption of the magnetometer 110 compared to an optical pulse sensor.

The pulse sensor 200 may further include a motion sensor 214 operatively coupled to the microcontroller 208. For example, the motion sensor 214 may include an accelerometer or a second magnetometer configured to sense an ambient magnetic field that is substantially stationary relative to movements of the user. In the "second magnetometer" embodiment, movement of the user through the earth's magnetic field and/or other ambient magnetic fields is sensed. In the second magnetometer embodiment, the pulse sensor 200 may further include a magnetic shield 216 configured to shield the second magnetometer 214 from changes in magnetic field strength corresponding to movement of the magnet 102.

In another embodiment, the motion sensor 214 may be integral with the magnetometer 110 and may include a magnetometer axis (e.g., along the y-axis into the plane of the drawing, FIGS. 2A and 2B) that is transverse to the plane of the magnetic axis 204. This approach results in partial confounding of movement with the pulse motion of the magnet(s) 102, but may be useful for parts reduction. In another embodiment, the motion sensor 214 may be integral with the magnetometer 110, and the motion sensor 214 may include an accelerometer. In an embodiment, the motion sensor 214 can be integral with the magnetometer 110. For example, the magnetometer 110 can sense magnetic fields (e.g., the earth's magnetic field) along a magnetic sensor axis that is transverse to the magnetic axis 204 (e.g., along the y-axis into the plane of the drawings FIGS. 2A and 2B). This approach may result in partial confounding of movement with the pulse motion of the magnet(s) 102, but can be useful for cost reduction. In another embodiment, the motion sensor 214 can be a portion of the health monitor sensor separate from the pulse sensor. For example, the motion sensor 214 can include an accelerometer, millimeter wave sensor, ultra-wideband sensor, radar and/or other devices or combinations thereof.

The pulse sensor 200 may further include a non-transitory computer-readable medium 218 contained within the microcontroller 208 or separate from the microcontroller 208 and operatively coupled to the microcontroller 208. In an embodiment, the non-transitory computer-readable medium 218 carries microcontroller 208 instructions configured to cause the microcontroller 208 to receive data or a signal from the magnetometer 110, receive detected movement information from the motion sensor 214, and filter the data or signal from the first magnetometer 110 responsive to the detected movement.

The filtering is described more fully in conjunction with FIG. 3 below.

The pulse sensor 200 may further include an electronic display 220 operatively coupled to the microcontroller 208. The microcontroller 208 may be configured to calculate a most likely pulse rate and to cause the electronic display 220 to display the most likely pulse rate.

The pulse sensor 200 may further include a radio 222 operatively coupled to or contained at least partially within the microcontroller 208. The microcontroller 208 may be configured to calculate a most likely pulse rate and to cause the radio 222 to transmit the most likely pulse rate, for example to a smart phone (not shown) running a fitness application that tracks the pulse rate.

Still referring to FIGS. 2A and 2B, according to an embodiment, the pulse sensor 200 includes a flexible membrane 114 configured to be held adjacent to a user's skin 202 at a location corresponding to an artery 104 subject to pulse movement, at least one magnet 102 disposed on the flexible membrane 114 and configured to move responsive to the pulse movement, and a magnetometer 110 configured to measure variations in a magnetic field from the at least one magnet 102 responsive to the pulse movement.

Other embodiments include positioning the magnetic axis 204 in a different orientation relative to the user's skin surface 202, than what is depicted in FIGS. 2A and 2B. For example, the magnet(s) 102 may be disposed to have a vertical magnetic axis, such that magnetic axis 204 is substantially normal transverse to the user's skin surface 202 (e.g. up to substantially perpendicular to the user's skin surface 202), and the magnetometer 110 may be configured to have a measurement axis 206 that measures variations in magnetic field strength along a vertical axis substantially parallel to the magnetic axis. Although advantages corresponding to overcoming z-axis precision, signal-to-noise, or size may be lost, such a (normal) alignment of magnetic axis and magnetic measurement axis was found by the inventors to work.

Referring to FIG. 2B, in an embodiment, the magnets 102a, 102b may be disposed to have antiparallel magnetic poles 204a, 204b. The inventors have found that arranging the magnetic poles 204a, 204b of the magnets 102a, 102b causes a magnetic field formed therebetween to have a large vertical (z-axis) component at the magnetometer 110. Accordingly, in an embodiment, the system 200, 201 may include a pair (or more) of movable magnets 102a, 102b having magnetic axes 204a, 204b arranged in opposition and a magnetometer 110 having a z-axis (either upward or downward) measurement axis 206.

In an embodiment, the at least one magnet 102 includes at least two magnets 102a, 102b, the at least two magnets 102a, 102b having magnetic axes 204a, 204b arranged antiparallel to one another. The magnetometer 110 may have a measurement axis 206 arranged perpendicular to the magnetic axes 204a, 204b of the at least two magnets 102a, 102b.

The motion sensor 214 is configured to detect movement of the human. The inventors have found that detected movement may provide data for inferring a change in heart rate. For example, an increased amount of movement may typically correspond to an increase in heart rate, and conversely a decreased amount of movement may typically correspond to a decrease in heart rate. The predictive nature of movement may be used to select from between several frequency candidates in successive signals from the magnetometer 110, any of which may correspond to the true heart rate.

The microcontroller 208 operatively coupled to the magnetometer 110 and the motion sensor 214 may include the non-transitory computer-readable medium 218 carrying microcontroller 208 instructions. The instructions may be selected to cause the microcontroller 208 to receive data or a signal from the magnetometer 110, receive detected movement information from the motion sensor 214, filter the data or signal from the first magnetometer 110 responsive to the detected movement, and output heart rate data corresponding to the filtered data or signal from the first magnetometer 110.

The approach to filtering is described in greater detail below.

FIG. 3 is a flow chart of a method 300 for detecting a heart rate, according to an embodiment. According to the method 300, a magnet is supported adjacent to the skin of a user in step 302. In step 304, a periodic physical impulse is received by the magnet responsive to arterial movement during systole and diastole. Proceeding to step 306, the magnet undergoes a periodic tilting motion responsive to the periodic physical impulse corresponding to systole and diastole. In step 308, a magnetometer detects, along an axis parallel to the person's skin, a periodic change in the strength of the magnetic field produced by the magnet. In step 310, a signal or data corresponding to a periodicity of the detected periodic change in the strength of the magnetic field is output. The output signal or data may correspond to a heart rate of the person.

Figure 4:
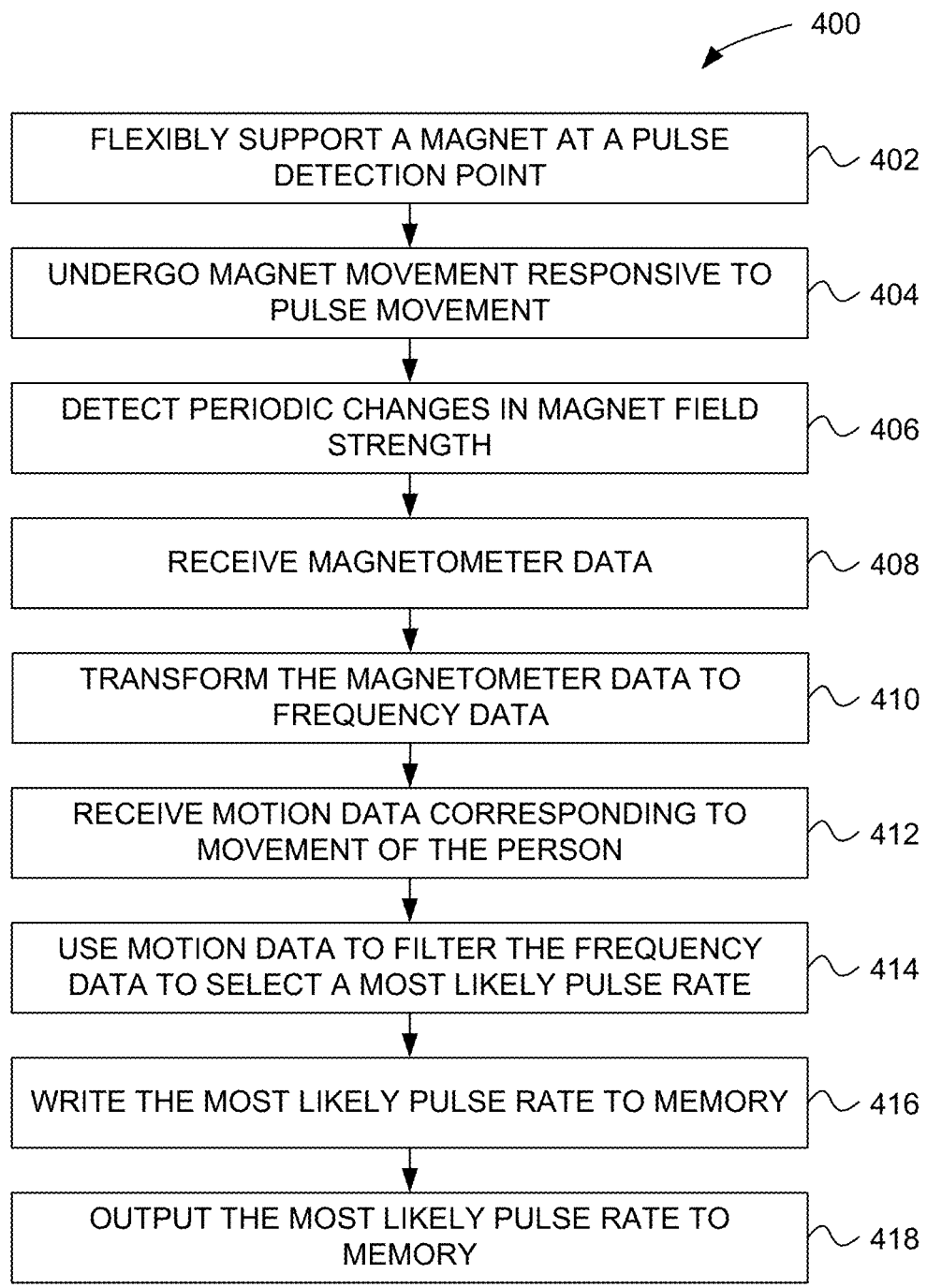
FIG. 4 is a flow chart of a method for tracking the heart rate of a person, according to an embodiment.

FIG. 4 is a flow chart of a method 400 for tracking the heart rate of a person, according to an embodiment. In step 402, a magnet is flexibly supported adjacent to a pulse detection location of a person. According to an embodiment, flexibly supporting a magnet adjacent to a pulse detection location of a person includes supporting a flexible membrane adjacent to the pulse detection location and supporting the magnet adjacent to an artery at the pulse detection location with the flexible membrane. For example, the flexible membrane may support the magnet adjacent to a pulse detection location on a wrist of the person. The inventors contemplate several alternative pulse measurement locations. In other examples, the flexible membrane may support the magnet adjacent to a pulse detection location on a foot or ankle of the person, adjacent to a pulse detection point on the neck of the person, adjacent to the temple of the person, near to a symphysis pubis of the person, or adjacent to a knee of the person. In other embodiments, the flexible membrane may support the magnet adjacent to a radial or ulnar artery, adjacent to a dorsalis pedis artery, adjacent to a posterior tibial artery, adjacent to a carotid artery, adjacent to a superficial temporal artery, adjacent to a femoral artery, or adjacent to a popliteal artery.

Proceeding to step 404, the magnet undergoes movement responsive to pulse movement of the person. As described above, the movement is responsive to expansion and contraction of an adjacent artery, and especially a peripheral artery, respectively corresponding to systolic and diastolic pressure pulses from the heart. As described above, several modes of movement and detection are contemplated. In a preferred embodiment, the magnet tilts responsive to arterial pulsing, and corresponding magnetic field strength is detected along an axis substantially parallel to the skin surface of the person.

In step 406, a magnetometer is operated to detect periodic changes in magnetic field strength from the magnet, the periodic changes in magnetic field strength corresponding to the movement of the magnet and the pulse movement of the person.

Proceeding to step 408, a microcontroller receives magnetometer data including the periodic changes in magnetic field strength from the magnet. The microcontroller can, as shown in step 410, transform the magnetometer data to produce frequency data. For example, transforming the frequency data may include performing a Fourier transform, such as a Fast Fourier Transform (FFT).

In step 412, the microcontroller receives motion data corresponding to movement of the person. The motion data may be produced by an accelerometer or another motion sensing device. In one example, the motion sensing device may include another magnetometer or another axis of the pulse-sensing magnetometer, wherein the motion data corresponds to motion of the person relative to far field sources, such as the earth's magnetic field.

In step 414, the motion data is used to filter the frequency data to select a frequency most likely to correspond to a pulse rate of the person. For example, using the motion data to filter the frequency data may include writing the frequency data to memory, writing the motion data to memory, comparing the motion data to previous motion data, determining the likelihood of a change in pulse rate responsive to the compared motion data, comparing the frequency data to previous frequency data, and identifying a high magnitude frequency domain point most likely to correspond to the pulse rate.

The method 400 may further include step 416, wherein the most likely pulse rate is written to memory, and step 418, wherein the most likely pulse rate is output. For example, step 418 may include wirelessly transmitting the most likely pulse rate to a personal electronic device. The personal electronic device may be configured to run a fitness or health application that uses the pulse rate. Additionally or alternatively, outputting the most likely pulse rate may include displaying the most likely pulse rate on an electronic display.

Figure 5A:
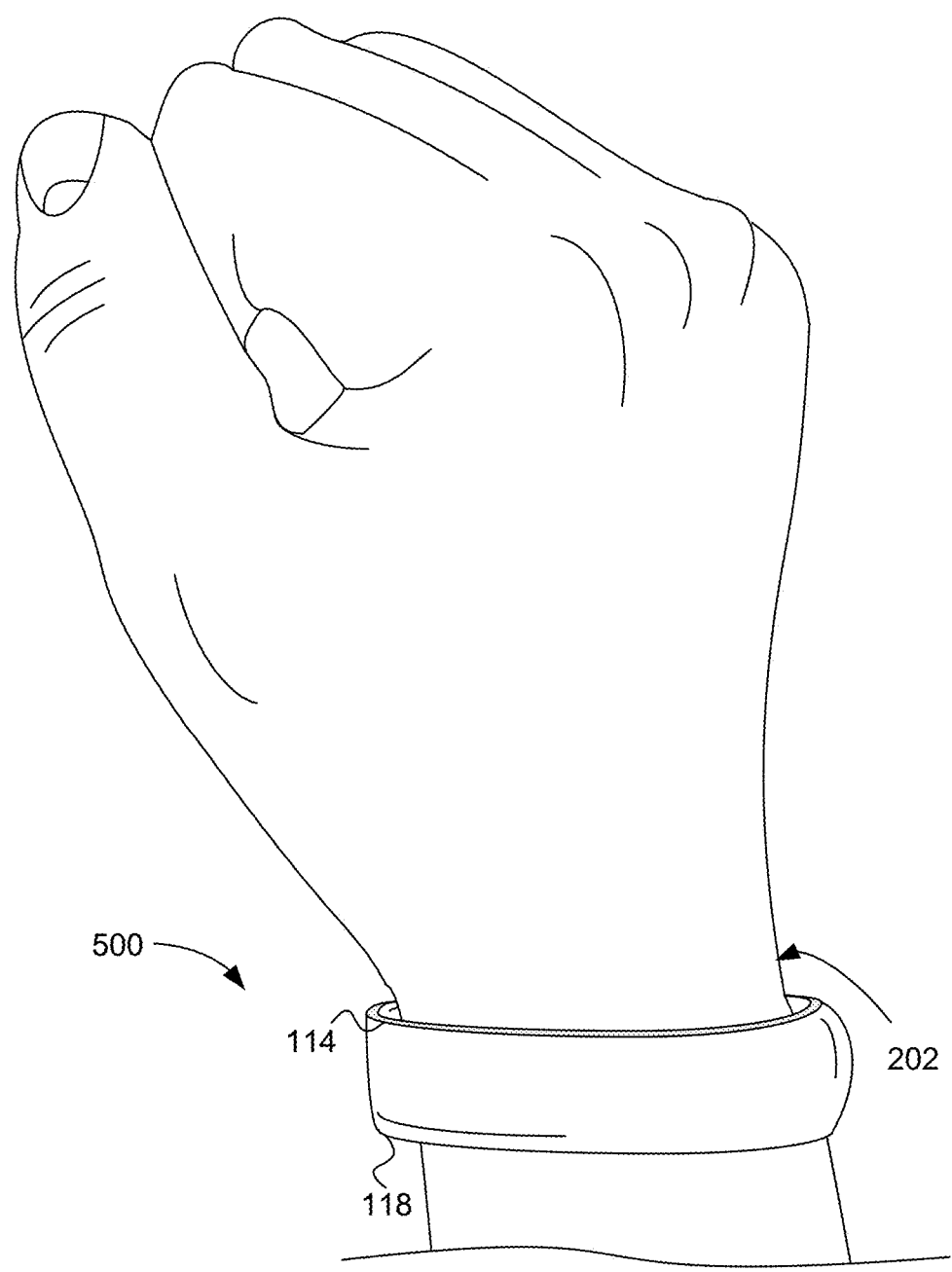
FIG. 5A is a perspective view of a pulse sensor configured as a wristband, according to an embodiment.

FIG. 5A is a perspective view of a pulse sensor 500 configured as a wristband, according to an embodiment. In another embodiment, the pulse sensor 500 may be configured as a hat or visor band configured to receive pulse movement from a human head. In another embodiment, the pulse sensor 500 may be configured as a sock or a shoe configured to receive pulse movement from a human ankle or foot. Other embodiments may include articles configured to be held against other areas of human skin subject to pulse movement.

Figure 5B:
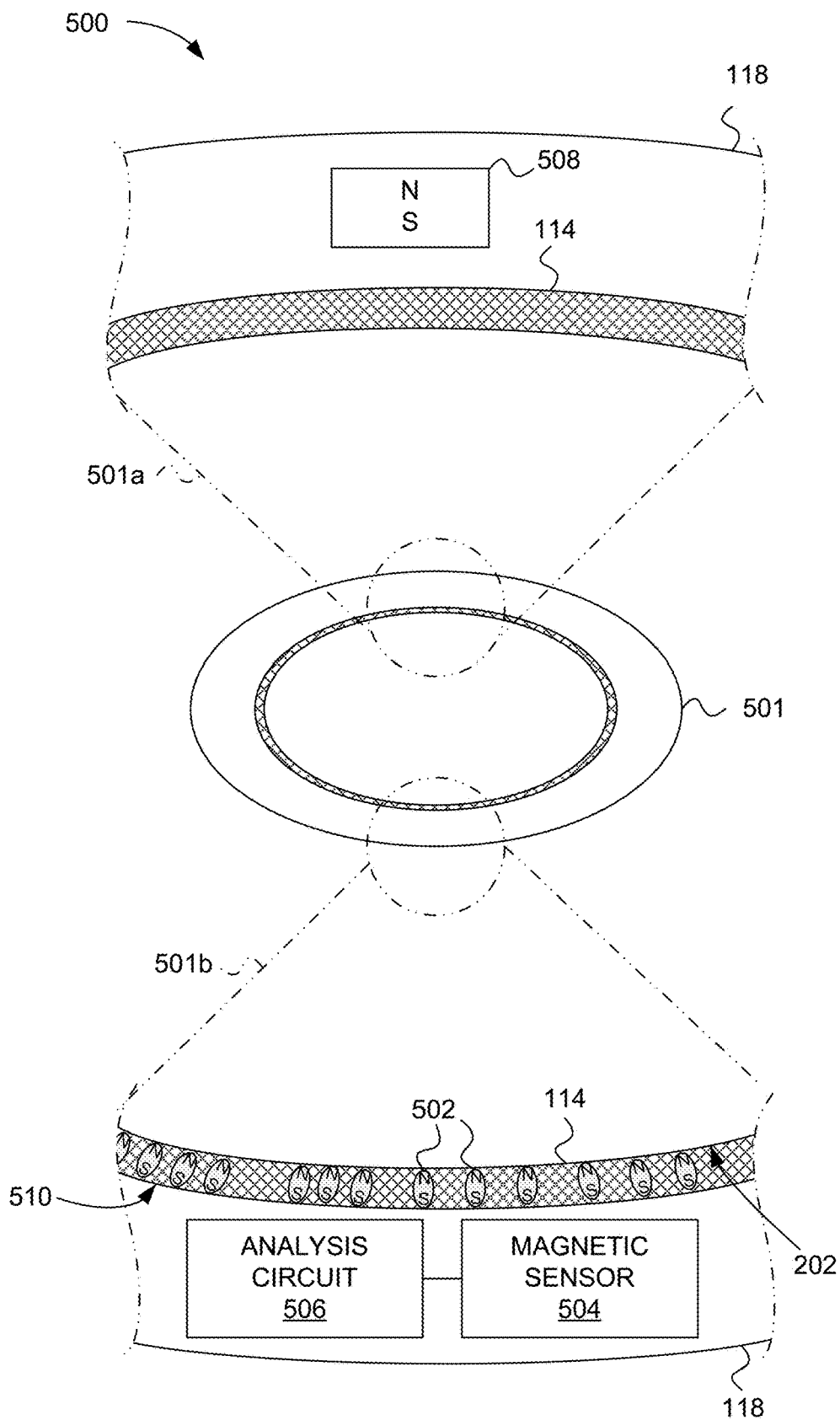
FIG. 5B is a sectional view and partial sectional views of the pulse sensor 100 of FIG. 5A, according to an embodiment.

FIG. 5B is a sectional diagram 501 with partial sectional views 501a, 501b of the pulse sensor 500 shown in FIG. 5A, according to an embodiment. With reference to FIGS. 5A and 5B, a flexible substrate 114 is configured for support against a human skin surface 202. The pulse sensor 500 includes a plurality of aligned magnetic dipoles 502 supported by the flexible substrate 114. A magnetic sensor 504 is configured to detect magnetic fields emitted by the plurality of magnetic dipoles 502. The magnetic sensor 504 may be a magnetometer, for example. An analysis circuit 506 is operatively coupled to the magnetic sensor 504.

The analysis circuit 506 may be configured to receive a sequence of data from the magnetic sensor 504. The sequence of data may include a component corresponding to changes in position of a portion of the plurality of magnetic dipoles 502, for example, the changes in position of the portion of the plurality of magnetic dipoles 502 corresponding to a pulse movement of the human skin surface 202. The analysis circuit 506 may be configured to output pulse chart data corresponding to the sequence of data, to determine a heart rate and output the heart rate to a data register.

Optionally, the pulse sensor 500 may include a poling magnet 508 configured to pole the plurality of magnetic dipoles 502 into alignment. The poling magnet 508 may include a permanent magnet configured to maintain a substantially constant magnetic field across each of the plurality of magnetic dipoles 502. Alternatively, the poling magnet 508 may include an electromagnet. The electromagnet may be configured to maintain a substantially constant magnetic field across each of the plurality of magnetic dipoles 502 or may be configured to apply a periodically reversing poling field to the plurality of magnetic dipoles 502.

The plurality of magnetic dipoles 502 may include high coercivity magnetic particles whose pole orientations are aligned by an external magnet as they are cured into the flexible substrate 114 while the flexible substrate 114 is curing. In this case, the plurality of magnetic dipoles 502 are held in magnetic alignment by a cross-linked component of the flexible substrate 114. Additionally or alternatively, the plurality of magnetic dipoles 502 may be placed in pole aligned orientation by assembling them onto the flexible substrate 114 with a pick-and-place machine.

Alternatively, the plurality of magnetic dipoles 502 may include low coercivity ferromagnetic particles whose pole orientation is induced by an applied magnetic field. As described above, the pulse sensor 500 may include the poling magnet 508 configured to hold the plurality of ferromagnetic particles in magnetic alignment as magnetic dipoles 502. The poling magnet 508 may include a permanent magnet. The poling magnet 508 may be configured to maintain a substantially constant magnetic field across each of the plurality of magnetic dipoles 502. The poling magnet 508 may include an electromagnet. The electromagnet may be configured to apply a field with periodically reversing magnetic pole to the plurality of magnetic dipoles 502.

The sequence of data output from the magnetic sensor 504 to the analysis circuit 506 may include data corresponding to the periodically reversing magnetic field. The analysis circuit 506 may convert the sequence of data to baseband data that includes the component corresponding to changes in position of the portion of the plurality of magnetic dipoles 502 corresponding to a pulse movement of the human skin surface 202. The plurality of magnetic dipoles 502 may be configured to magnetically rotate responsive to the periodically reversing poling field and to maintain magnetic polarity in the periodically reversing poling field.

The plurality of magnetic dipoles 502 may be held in alignment by a cross-linked component of the flexible substrate 114. The alignment of the magnetic dipoles 502 may be formed by poling the magnetic dipoles 502 carried by a precursor of the flexible substrate 114 and cross-linking the cross-linked component to hold the plurality of magnetic dipoles 502 in net magnetic alignment. Additionally or alternatively, the plurality of magnetic dipoles 502 may be held in alignment by the flexible substrate 114 and/or assembled onto the flexible substrate 114 by a pick-and-place machine.

The magnetic dipoles 502 may carry a net magnetic alignment as a group. Individual magnetic dipoles may carry respective magnetic axes that differ from the net magnetic alignment. The magnetic dipoles 502 may be aligned along a Cartesian axis, aligned along respective radial axes, aligned along hyperbolically varying axes in at least one plane, and/or aligned with respective axes that are substantially normal to the flexible substrate 114.

The magnetic sensor 504 may include a sensor configured to sense a magnetic field along an axis at least periodically corresponding to a magnetic axis of the magnetic dipoles. Optionally, the magnetic sensor 504 may be configured to sense magnetic field strength along a plurality of axis. For example, the magnetic sensor 504 may include an X-axis magnetic sensor configured to sense a magnetic field component along an X-axis, a Y-axis magnetic sensor configured to sense a magnetic field component along a Y-axis, and a Z-axis magnetic sensor configured to sense a magnetic field component along a Z-axis. The X-, Y-, and Z-axes may be defined with respect to a sensor circuit assembly and/or may be defined with respect to the plurality of aligned magnetic dipoles 502.

The magnetic sensor 504 may include at least one sensor aligned relative to the aligned magnetic dipoles 502 and a magnetic sensor array configured to sense magnetic field components at a plurality of locations in a sensor array.

The magnetic sensor 504 may be configured to sense one or more magnetic field components less than $10^{-3}$ as strong as the earth's magnetic field. In another embodiment, the magnetic sensor 504 may be configured to sense one or more magnetic field components less than $10^{-6}$ as strong as the earth's magnetic field.

The magnetic sensor 504 may be arranged as a plurality of sensor modules, each sensor module being configured to sense a magnetic field along a plurality of sensing axes.

The analysis circuit 506 may be configured to receive a sequence of data from the magnetic sensor 504. Each datum in the sequence of data may correspond to magnetic field strength along each of three axes. The analysis circuit 506 may be configured to transform each datum by calculating a square root of a sum of squares of the data corresponding to the magnetic field strength along each of three axes. Additionally or alternatively, the analysis circuit 506 may be configured to output the transformed data to a data buffer.

The pulse sensor 500 may include the housing 118 configured to carry the flexible substrate 114, the magnetic sensor 504, and the analysis circuit 506. The housing 118 may be configured to be worn around a human wrist, as shown in FIG. 5A. The flexible substrate 114 may be elastomeric. The housing 118 may include a suspension, such as hydrogel, operatively coupled to the flexible substrate 114, the suspension being configured to urge the flexible substrate 114 against the human skin surface 202.

The pulse sensor 500 may further include an elastomeric foam disposed to press against an outside surface 510 of the flexible substrate 114, the elastomeric foam being configured to urge the flexible substrate 114 carrying the plurality of magnetic dipoles 502 against the human skin surface 202. In an embodiment, the magnetic sensor 504 may include a magnetometer.

FIG. 6 is a flowchart showing a method 600 for detecting a human pulse, according to an embodiment. The method 600 begins with step 602, in which a flexible substrate carrying aligned magnetic dipoles is supported (e.g., held) against a human skin surface. The flexible substrate is particularly supported against a portion of the human skin surface subject to motion caused by a human pulse. For example, the flexible substrate with magnetic dipoles may be supported against an artery in a wrist, or against a carotid artery in the neck.

Optionally, the method 600 may include step 604, wherein the plurality of magnetic dipoles are held in net magnetic alignment by supporting a magnet near the plurality of magnetic dipoles. The magnet forms a magnetic poling field across the plurality of magnetic dipoles that causes the magnetic dipoles to rotate into alignment. According to an embodiment, aligned magnetic dipoles may be formed as net magnetic dipoles. In other words, the magnetic dipoles may be aligned to an average axis, but individual magnetic particles (dipoles) may be off-axis or even antiparallel to the average axis.

In alternative to step 604, the magnetic dipoles may be aligned during manufacture of the pulse sensor. For example, the dipoles may be poled while a polymer is cross-linked around the dipoles to hold them in place. Alternatively, the dipoles may be applied to the flexible substrate in alignment, such as by a pick-and-place machine.

Proceeding to step 606, physical movement of a portion of the magnetic dipoles from the human skin surface is received, the physical movement being a pulse movement of the human skin surface.

In step 608, magnetic field data is sensed. For example, the magnetic field data may include measurement of a time sequence of magnetic fields. The time sequence may include a component corresponding to motion of the aligned magnetic dipoles caused by the human pulse.

Proceeding to step 610, the magnetic field data is transformed to heartbeat data corresponding to the sensed human pulse. The method 600 may include step 612, wherein the heartbeat data is converted to a human heart rate.

A health monitor sensor, unless context dictates otherwise, includes a sensor that is capable of detecting a signal at a peripheral artery proportional to instantaneous blood flow and of outputting data indicative of a plurality of artery expanded states (e.g. instantaneous cross-sectional areas, instantaneous diameters, or the like) similarly to a skilled person detecting a pulse at the location(s). Embodiments described herein make use of a modulation sensitive pulse sensor. Modulation sensitive pulse sensors may include strain or pressure sensors, ultrasound transceiver sensors, photoplethysmography transceiver sensors, or magnetic sensors, as further described herein.

Embodiments of the health monitor sensor described herein include a pulse sensor that has a first portion held conformal to pulsations of the artery expressed as movements of the skin of the wearer. A second portion of the pulse sensor is configured to measure periodic displacement of the first portion relative to the wearer's body.

Figure 10:
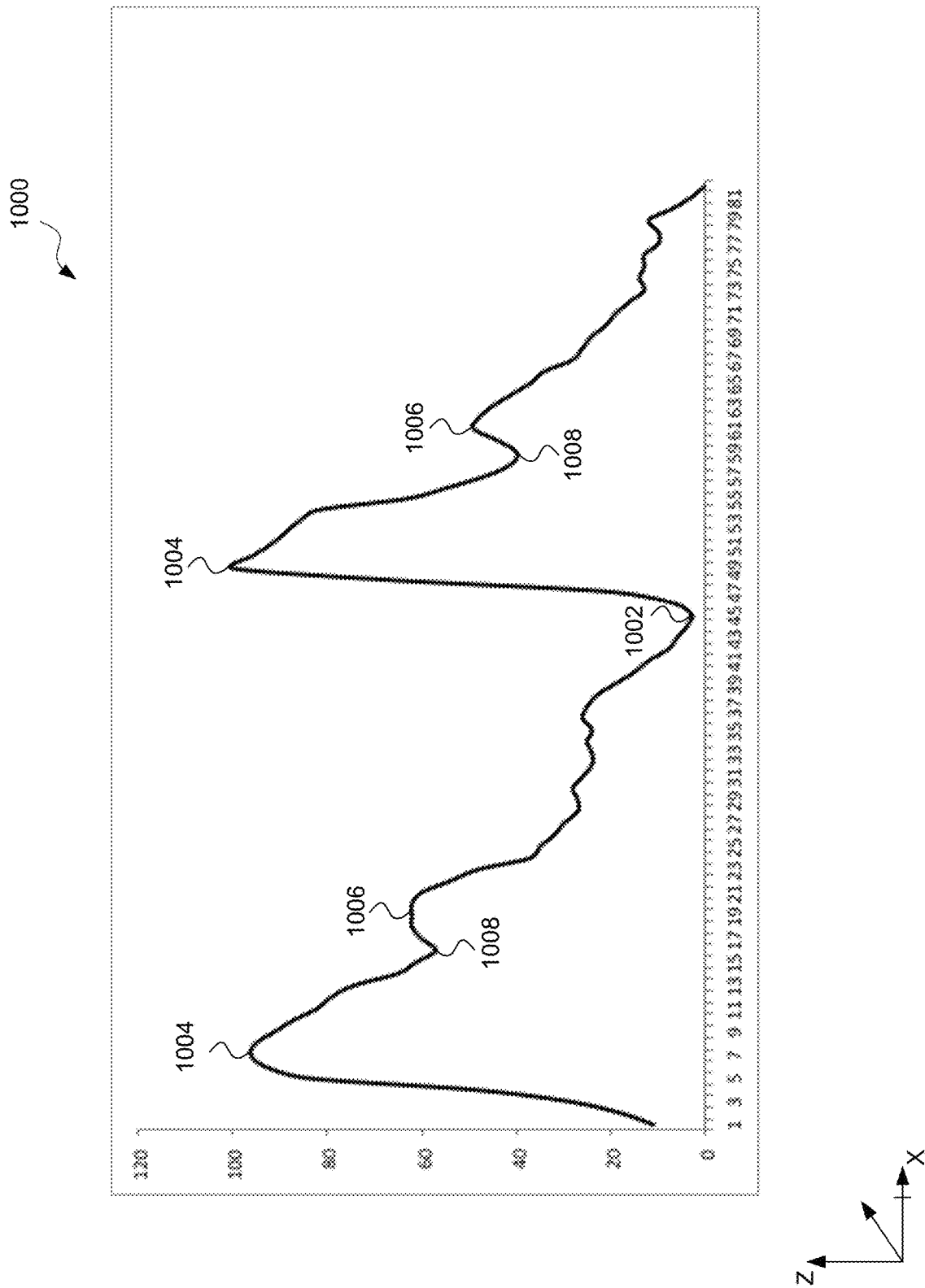
FIG. 10 is a diagram of a pulse wave corresponding to data generated by a prototype pulse sensor described in conjunction with FIGS. 2A and 2B, according to an embodiment.

FIG. 10 is a diagram of a pulse wave 1000 corresponding to data generated by a prototype pulse sensor described in conjunction with FIGS. 2A and 2B.

Referring to FIG. 10, FIG. 2A corresponds to a portion 1002 of a pulse wave 1000 between heartbeats when the artery 104 is contracted. The magnet(s) 102 tend to lie in plane with the user's skin 202.

The inventors have discovered that a ratio between the (vertical axis) value of the systolic pressure 1004 to the value of the diastolic hump 1006 is indicative of the state of hydration of a wearer of the sensor.

In yet other embodiments, a number of magnets 102 may be disposed to respond to pulse movement at a plurality of locations along a peripheral artery 104.

According to an embodiment, the pulse sensor 200 may include sensors other than magnetic sensors (e.g., magnetometer 110) for sensing the pulse rate, modulation, or blood flow rate in a peripheral artery. For example, the pulse sensor 200 may include one or more of piezo-electric sensors, piezo-resistive sensors, capacitive sensors, or other kinds of sensors suitable for detecting parameters of a peripheral artery. Those of skill in the art will recognize, in light of the present disclosure, that sensors other than those described herein may be used in accordance with principles of the present disclosure. Such other sensors may fall within the scope of the present disclosure.

Figure 11:
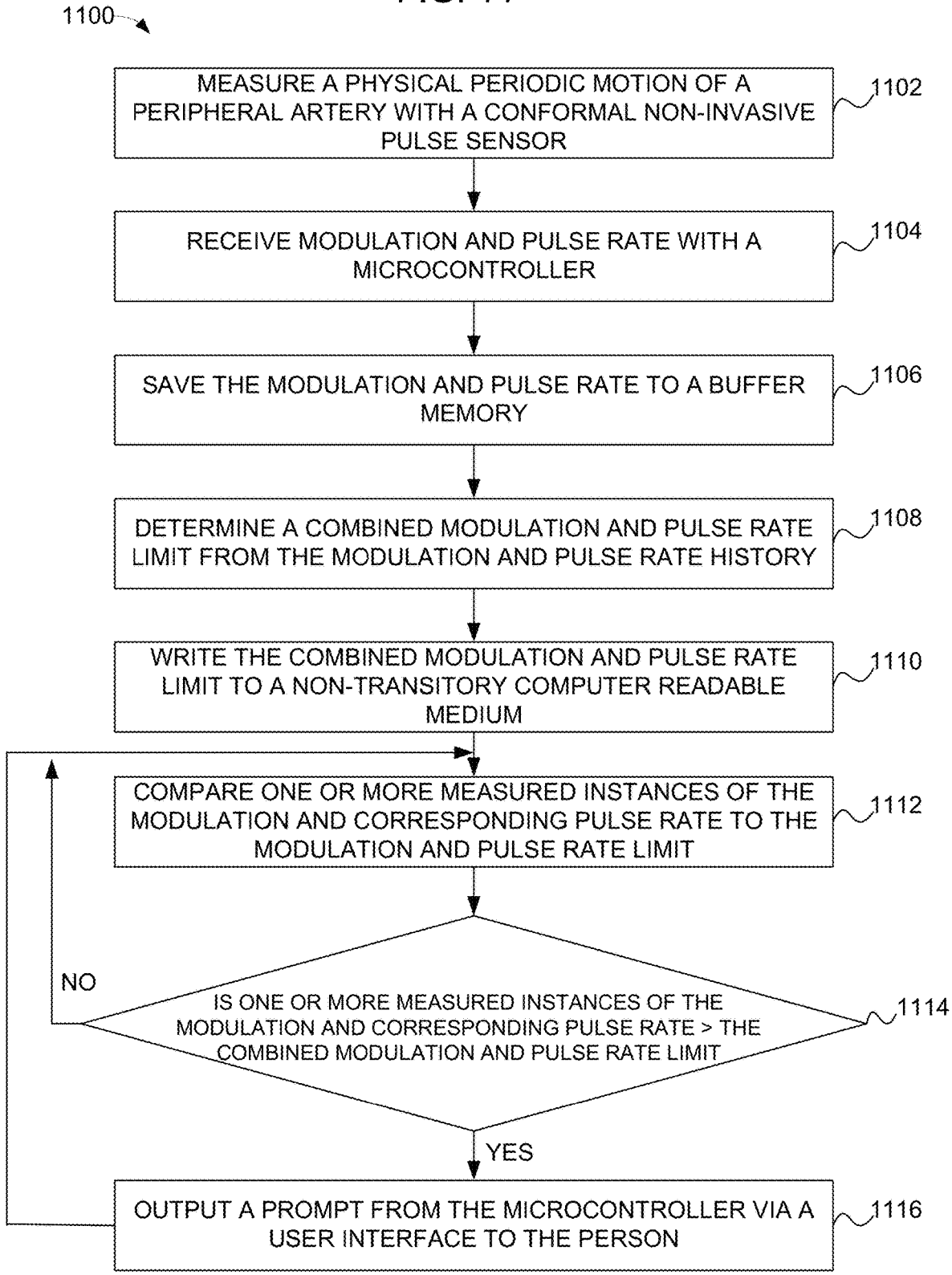
FIG. 11 is a flow chart of a method for monitoring the hydration of a person, according to an embodiment.

FIG. 11 is a flow chart of a method 1100 for monitoring the hydration of a person, according to an embodiment. The method 1100 begins at step 1102, which includes measuring a physical periodic motion corresponding to a peripheral artery with a pulse sensor to determine pulse data, each measured physical periodic motion corresponding to a sequence of instantaneous arterial size estimates or derivatives thereof. The pulse data (which may include a modulation and a pulse rate) is then output. For example, the measurements may be performed by a pulse sensor akin to the pulse sensor 200 described in conjunction with FIGS. 2A and 2B. According to an embodiment, each instance of modulation and pulse rate data may be obtained from a series of measurements of a magnetic field strength, e.g. as the field strength produced by one or more magnets that are displaced by the physical pulsations of the artery. The field strength is measured at a frequency that is a sufficiently small fraction of a pulse period to produce a waveform corresponding to changing diameters of the artery during the pulse period, and for sufficient duration to average across a plurality of periods.

Referring to FIG. 10, the modulation data for each pulse include the sequence of magnetic field strengths over the duration of the pulse period as it passes the sensor as a wave. The differences (or average difference) between maximum and minimum magnetic field strengths are used to define the magnitude of systolic expansion 1004 across the periodic response of the artery (optionally, averaged along the plurality of periods). The shape and magnitude of the diastolic hump 1006 is included in the modulation data, the value being determined by finding the local maximum between a local minimum 1008 (dicrotic notch) following the systolic peak 1004 and the overall minimum 1002.

The inventors have discovered that the ratio of systolic maximum 1004 to diastolic hump maximum 1006 is covariant with hydration, at least over a hydration range. This relationship is used, according to embodiments, to infer a state of hydration of the measured individual.

In an embodiment, referring again to FIG. 11, the method 1100 includes detecting periodic pulsations at a plurality of distances along an artery.

Referring again to FIG. 11, proceeding to step 1104, one or more instances of pulse data are received with a programmable hardware device (e.g., microcontroller). In step 1106, the microcontroller writes the pulse data to a memory device as an instant in an arterial pulsation history. Optionally, the microcontroller may calculate a function of the combined modulation and pulse rate (as described below) for each instance of the modulation and pulse rate pair. In this case, separately saving the actual modulation and actual pulse rate may be omitted. It will be understood that such a calculation and omission falls within the definition of "saving the modulation and pulse rate into a buffer memory." The steps 1102 to 1106 can, in an embodiment, be performed asynchronously with other steps of the method 1100. The arterial pulsation history is then read by the microcontroller.

In step 1108, the microcontroller may determine at least one limit including at least one of a pulse wave modulation value, a pulse rate value, and a blood flow value from the arterial pulsation history. Optionally, step 1108 may include determining separate limits for pulse rate and modulated difference between systolic peak and diastolic hump. (Under a condition of dehydration, the pulse rate increases and the difference in height between the systolic peak and diastolic hump decreases.) In another embodiment, step 1108 may include determining an overall blood flow by integrating or summing the total area under the pulse wave curve over a plurality of periods, referred to as blood flow herein. (Under a condition of dehydration, pulse rate increases but blood flow decreases.) In another embodiment, step 1108 may include determining both the modulated difference between systolic peak and diastolic hump and blood flow. The method 1100 may include determination of a function (that may be embodied as a look-up table, or LUT) that carries both a combined variable limit and separate single variable limits. For ease of reference, any combination of single variable and multiple variable limits may be referred to as limits, herein. In an embodiment, the modulation corresponds to a difference in ratio between systolic peak and diastolic hump in expansion of the peripheral artery based on the pulse sensor. The method 1100 further includes identifying the diastolic hump as a local maximum in expansion of the peripheral artery between a local minimum corresponding to a dicrotic notch and an overall minimum of a diameter of the peripheral artery as indicated by the pulse sensor. In an embodiment, the systolic peak corresponds to an overall maximum expansion of the peripheral artery as indicated by the pulse sensor.

In step 1110, the at least one limit is written to a non-transitory computer readable medium. For example, the buffer memory may form a portion of the non-transitory computer readable medium.

In an embodiment, proceeding from step 1110, one or more new pulse data sets is received, and at least one new variable value from the one or more new pulse data sets is calculated. Periodically (and optionally asynchronously with the pulse and modulation pair periodicity), referring to step 1112, the programmable hardware device (microcontroller) may compare the at least one new variable value to the at least one limit. Step 1114 is a decision step, wherein if the variables are within limits, the method 1100 may loop back to step 1112. If the variables are not within limits, the method proceeds to step 1116. In step 1116, the microcontroller outputs a prompt via a user interface to the person. Step 1116 is executed only if a predetermined number of instances of the at least one new variable falls outside the at least one limit. The method 1100 further may include determining and writing at least one new value of the at least one limit as a function of one or more instances of the one or more new pulse data sets. The at least one new value of the at least one limit may be a function of at least a portion of at least one prior value of the at least one limit.

Outputting the prompt may take various forms. In one example, the apparatus includes a visual display such as an LED that normally pulses green approximately synchronously with the person's pulse. When the limits are violated, the microcontroller may cause the LED to pulse amber. Optionally, the variables may include different levels of limits. A more severe violation of the limits may cause the microcontroller to cause the LED to flash red. Other types of visual, audible, and haptic user interfaces for issuing the prompt may equivalently fall within meaning of "prompt."

Various related embodiments are contemplated by the inventors.

In one embodiment, comparing the at least one new variable value to the at least one limit in step 1112 includes comparing at least three successive measured instances of the at least one new variable value to the at least one limit. Similarly, outputting a prompt from the microcontroller via a user interface to the person if the predetermined number of instances of the at least one new variable value falls outside the at least one limit may include outputting the prompt if and only if each of the at least three successive instances of the at least one new variable value falls outside the at least one limit.

As indicated above, measuring a physical periodic motion corresponding to a peripheral artery with a pulse sensor, in step 1102, may include supporting one or more magnets on a flexible substrate adjacent to the person's skin such that the peripheral artery lies subjacent to the one or more magnets; and detecting a magnetic field variation produced by the one or more magnets responsive to physical pulsations received from the subjacent peripheral artery with a magnetic sensor.

The inventors contemplate a variety of approaches to determining the limits. For example, step 1108 may include computing a standard deviation of instances of the arterial pulsation history and setting the at least one limit as two standard deviations greater than a mean arterial pulsation history value. Additionally or alternatively, step 1108 may include computing a slope variable of a function of instances of the at least one value, and setting the at least one limit as a derivative of the slope variable times a constant greater than one. I In an embodiment, the prompt may indicate that the person is dehydrated. The method 1100 further may include outputting the prompt if the pulse rate falls outside the pulse rate limit and if the modulation falls outside the modulation limit.

According to an embodiment, a non-transitory computer readable medium carrying computer executable instructions configured to cause a portable device to execute a method including the steps of measuring a physical periodic motion of a peripheral artery with a pulse sensor, each measured physical periodic motion including a modulation and a pulse rate, and receiving the modulation and pulse rate with a microcontroller and saving the modulation and pulse rate to a buffer memory as a modulation history and pulse rate history. The method includes determining, with the microcontroller, a modulation, estimated instantaneous blood flow rate and pulse rate limit from the modulation and pulse rate history, and writing the modulation, blood flow rate and pulse rate limit to a non-transitory computer readable medium. The method includes comparing, with the microcontroller, one or more measured instances of the modulation, blood flow rate and corresponding pulse rate to the modulation, blood flow rate and pulse rate limit, and outputting a prompt from the microcontroller via a user interface to the person if the one or more measured instances of the modulation, blood flow rate and pulse rate falls outside the modulation, blood flow rate and pulse rate limit.

In an embodiment, comparing the one or more measured instances of the modulation, blood flow and corresponding pulse rate to the modulation, blood flow and pulse rate limit further includes comparing at least three successive measured instances to the combined modulation and pulse rate limit. Outputting a prompt from the microcontroller via a user interface to the person if the one or more measured instances of the modulation, blood flow and pulse rate falls outside the modulation, blood flow and pulse rate limit further includes outputting the prompt if and only if each of the at least three successive measured instances falls outside the modulation, blood flow and pulse rate limit.

In an embodiment, measuring a physical periodic motion of a peripheral artery with a pulse sensor further includes supporting one or more magnets on a flexible substrate adjacent to the person's skin such that the peripheral artery lies subjacent to the one or more magnets, and detecting a magnetic field variation produced by the one or more magnets responsive to physical pulsations received from the subjacent peripheral artery with a pulse sensor.

In an embodiment, determining, with the microcontroller, the modulation and pulse rate limit from the modulation and pulse rate history further includes computing a standard deviation variable of a function of instances of modulation and blood flow rate divided by corresponding pulse rate, and setting the modulation and pulse rate limit as two standard deviations greater than a mean function value. Alternatively, determining, with the microcontroller, the modulation, blood flow and pulse rate limit from the modulation and pulse rate history further includes computing a slope variable of a function of instances of modulation and blood flow rate divided by corresponding pulse rate, and setting the modulation, blood flow and pulse rate limit as a derivative of the slope variable times a constant greater than one.

In an embodiment, the prompt indicates that the person is dehydrated. The method may further include outputting the prompt if the pulse rate falls outside the pulse rate limit and if the modulation falls outside the modulation limit.

In an embodiment, the modulation corresponds to a difference or ratio between systolic peak and diastolic hump corresponding to respective expansion of the peripheral artery. In another embodiment, the method further includes identifying the diastolic hump as a local maximum in expansion of the peripheral artery between a local minimum corresponding to a dicrotic notch and an overall minimum of a diameter of the peripheral artery as indicated by the pulse sensor. The systolic peak may correspond to an overall maximum expansion of the peripheral artery as indicated by the pulse sensor.

According to an embodiment, a method includes generating, with a pulse sensor positioned adjacent to a peripheral artery of a person, pulse sensor signals indicative of movement of the peripheral artery, calculating, with a digital processor, a pulse rate and a modulation of the peripheral artery based on the pulse sensor signals, and comparing, with the digital processor, the pulse rate and the modulation to reference pulse rates and reference modulations. The method includes determining, with the digital processor, a state of hydration of the person based on the comparison of the pulse rate and modulation to the reference pulse rates and reference modulations, and outputting an alert to the user if the state of hydration corresponds to the person being dehydrated.

In an embodiment, the modulation corresponds to a difference between systolic peak and diastolic hump in expansion of the peripheral artery as indicated by the sensor signals. In another embodiment, the modulation corresponds to a ratio between systolic peak and diastolic hump in expansion of the peripheral artery as indicated by the sensor signals.

In an embodiment, the method further includes determining that the person is dehydrated based on an increase in pulse rate compared to the reference pulse rate and a decrease in modulation compared to the reference modulation. In an embodiment, the method further includes generating, with the digital processor, the reference pulse rate and modulation based on previous motion of the peripheral artery as indicated by sensor signals previously generated by the pulse sensor.

Figure 12:
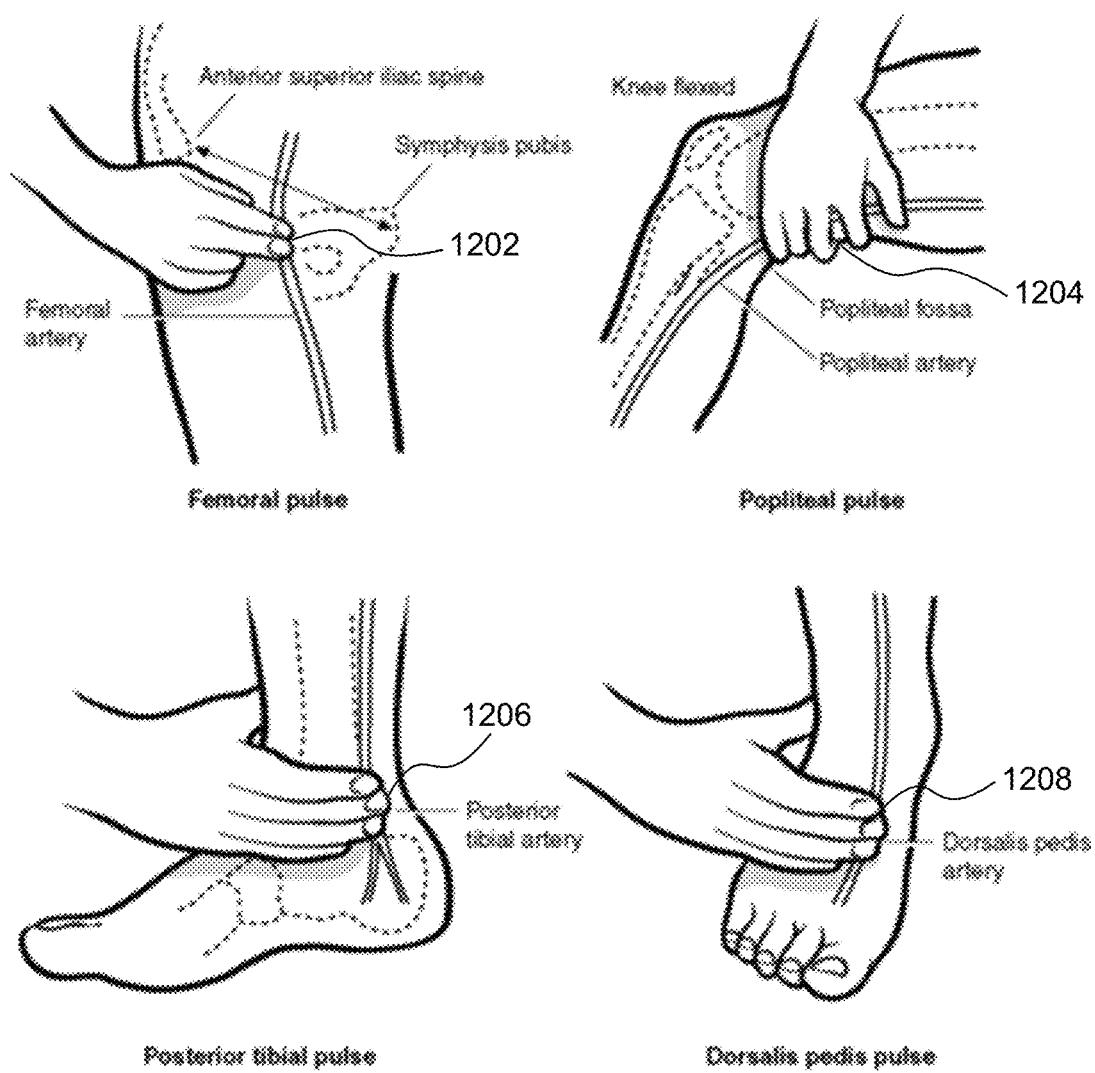
FIG. 12 illustrates optional locations for supporting a pulse sensor against respective arteries, according to embodiments.

FIG. 12 illustrates optional locations 1202, 1204, 1206, 1208 for supporting a pulse sensor against respective arteries, according to embodiments.

In an embodiment, a pulse sensor may detect a femoral pulse near a symphysis pubis of the wearer by positioning the pulse sensor to detect blood pulsation in the femoral artery 1202. For example, an undergarment or garment (not shown) positioned adjacent to the femoral artery 1202 may carry a pulse sensor. In the case of a magnetic pulse sensor, the undergarment or garment may support a flexible surface in contact with the skin surface, the flexible surface carrying a magnet subject to movement responsive to pulse palpations.

In an embodiment, a pulse sensor may detect a popliteal pulse at a knee of the wearer by positioning the pulse sensor to detect blood pulsation in the popliteal artery 1204. For example, a knee brace, knee protector, or garment (not shown) positioned adjacent to the popliteal artery 1204 may carry a pulse sensor. In the case of a magnetic pulse sensor, the knee brace, knee protector, or garment may support a flexible surface in contact with the skin surface, the flexible surface carrying a magnet subject to movement responsive to pulse palpations.

In an embodiment, a pulse sensor may detect a posterior tibial pulse at a knee of the wearer by positioning the pulse sensor to detect blood pulsation in the posterior tibial artery 1206. For example, an ankle brace, sock, or shoe (not shown) positioned adjacent to the posterior tibial artery 1206 may carry a pulse sensor. In the case of a magnetic pulse sensor, the ankle brace, sock, or shoe may support a flexible surface in contact with the skin surface, the flexible surface carrying a magnet subject to movement responsive to pulse palpations.

In an embodiment, a pulse sensor may detect a dorsalis pedis pulse at a foot of the wearer by positioning the pulse sensor to detect blood pulsation in the dorsalis pedis artery 1208. For example, an ankle brace, sock, or shoe (not shown) positioned adjacent to the dorsalis pedis artery 1208 may carry a pulse sensor. In the case of a magnetic pulse sensor, the ankle brace, sock, or shoe may support a flexible surface in contact with the skin surface, the flexible surface carrying a magnet subject to movement responsive to pulse palpations.

EXAMPLES

Figure 7:
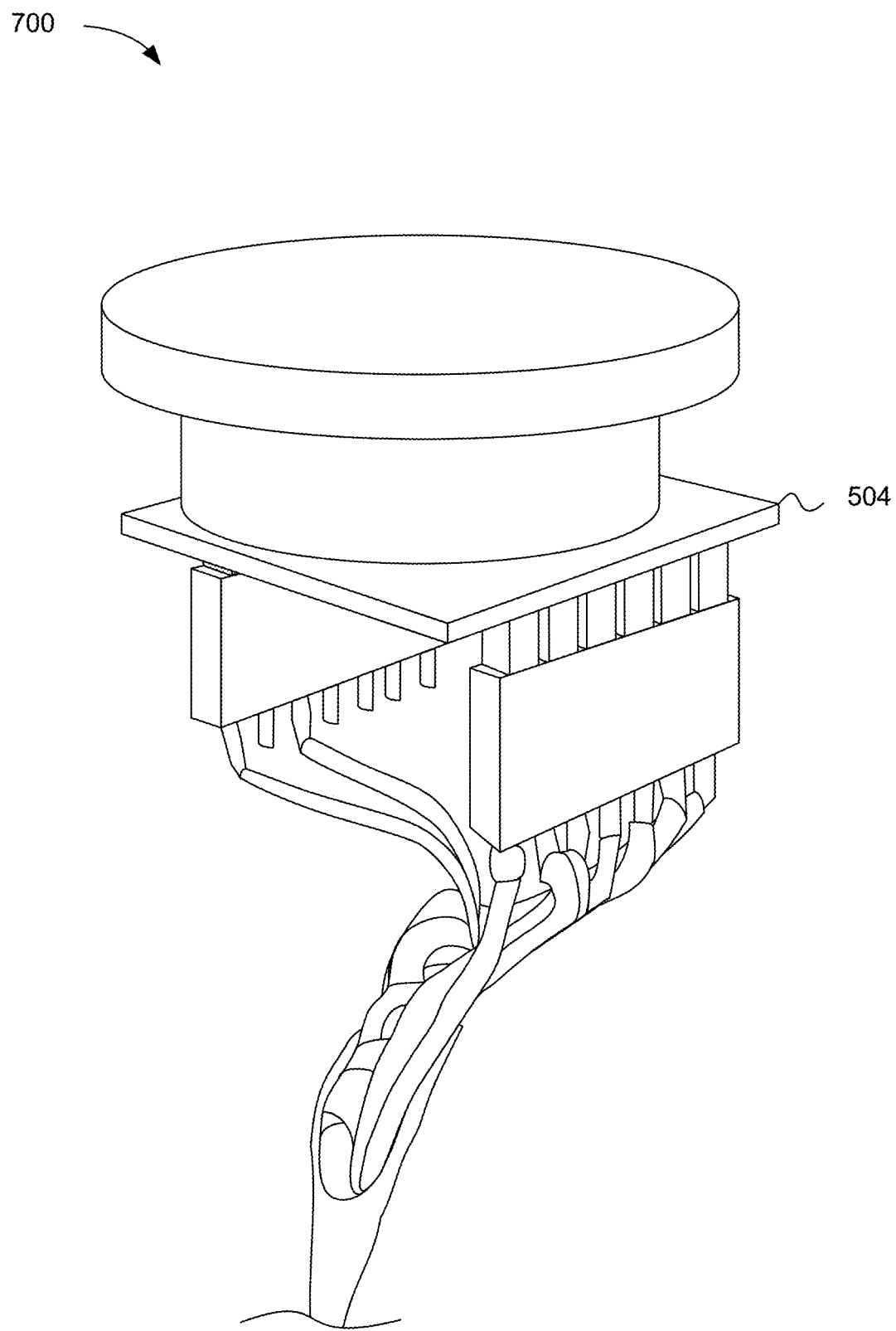
FIG. 7 is a view of a magnetic sensor used in an experiment reported in the Examples section, according to an embodiment.

Specific embodiments may be made by reference to the following examples:
Objective:
The objective of this study is to determine the technical feasibility of detecting human pulse at the wrist by means of magnetic sensors using a novel approach in which what is detected is perturbations to a reference magnetic field created by arterial palpation, i.e. the expansion/contraction of the artery cause by the bloods pulsation.
Approach:
The approach used in this study is to embed magnetic particles into an elastomeric substrate. The magnetic particles were formed by crushing a permanent magnet. The magnetic poles of the particles were aligned while the substrate was cured by exposing them to a strong external magnet. The resulting elastomeric membrane was then stretched across a PVC cylindrical cross-section and the magnetic sensor module was mounted on the opposite end of the PVC cylinder such that the sensor that is perpendicular to the membrane is approximately 2 mm from the membrane sensing down towards the membrane. A view of the sensor 504 is shown in FIG. 7. The sensor module 700 was connected by ribbon cable to a circuit board with power, control and I/O capabilities.

Figure 8:
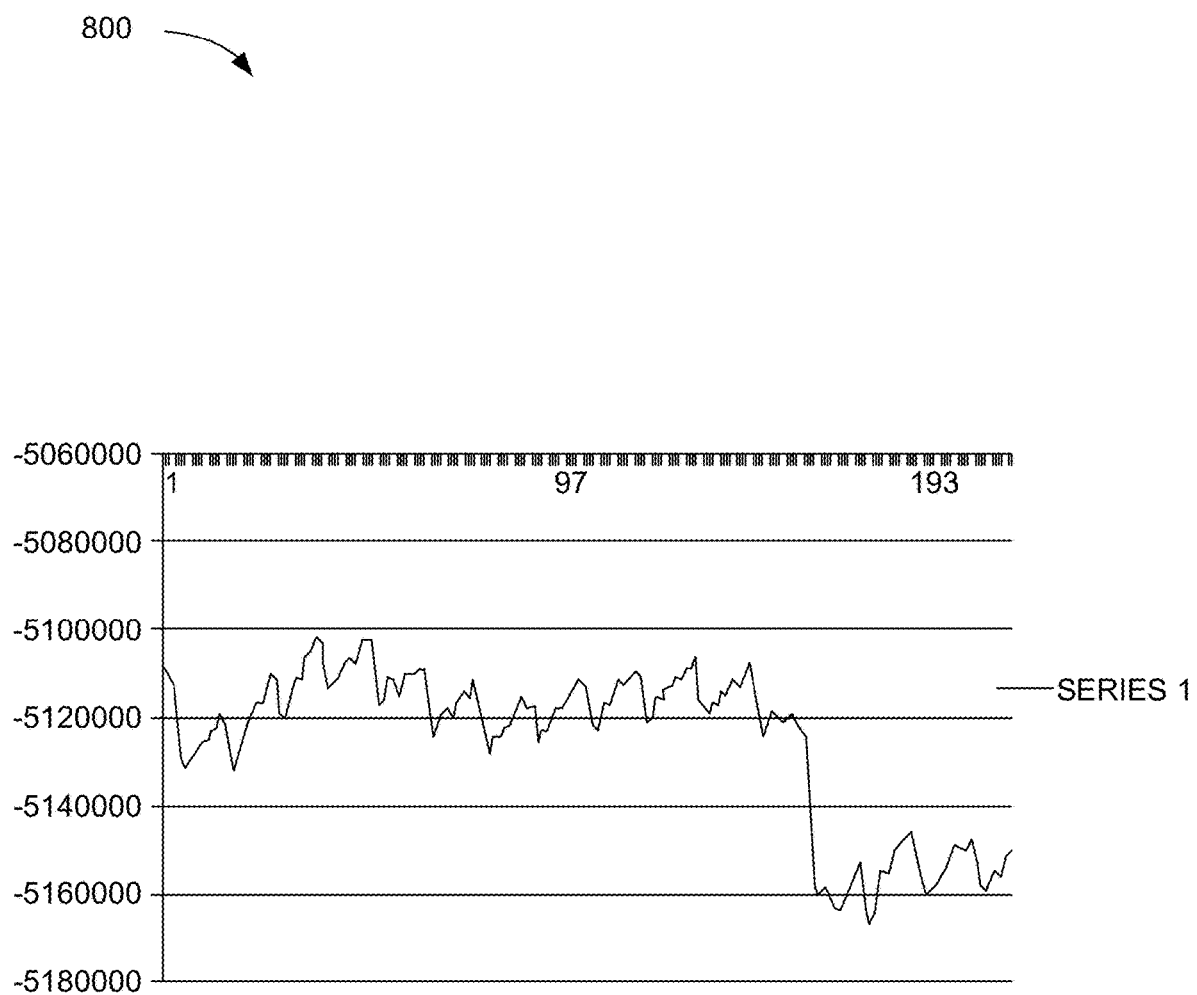
FIG. 8 is a plot of heartbeat data from the experiment described in the Examples section, according to an embodiment.
Figure 9:
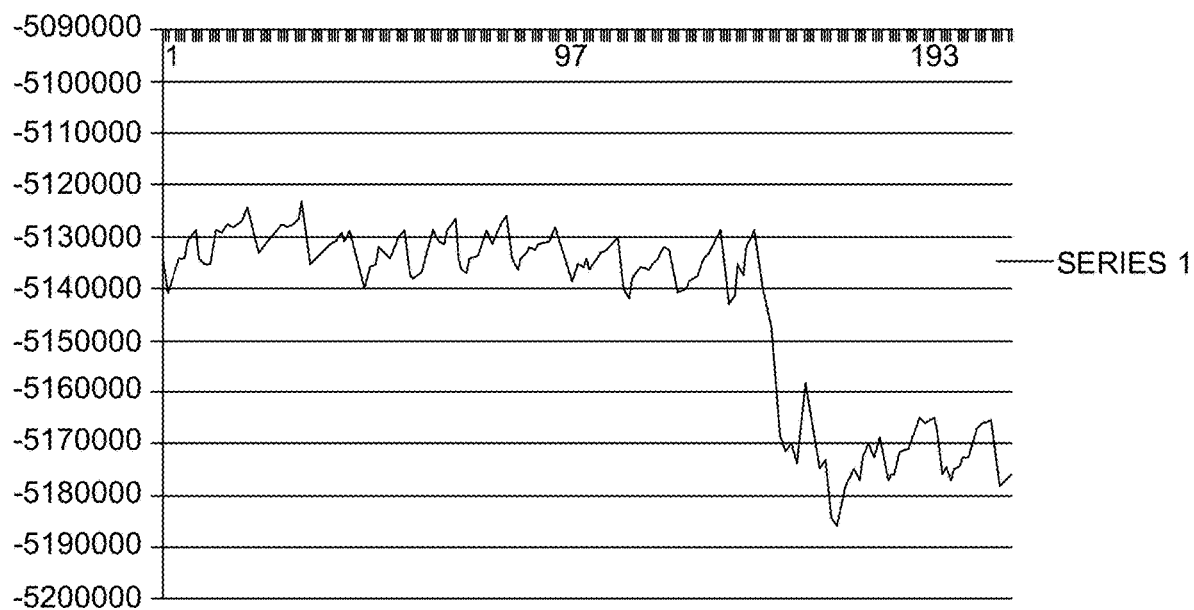
FIG. 9 is a second plot of heartbeat data from a second experimental run from the experiment described in the Examples section, according to an embodiment.

Results:

The sensor was pressed to the wrist at the radial artery. Samples were taken at a frequency 16.6 Hz for 12 s. The resulting time series clearly show a pulse averaging approximately 75 beats per minute. Data plots 800, 900 are shown in FIGS. 8 and 9. The pulse was then independently estimated to be approximately 75 bpm, which verified the data.

While various aspects and embodiments have been disclosed herein, other aspects and embodiments are contemplated. The various aspects and embodiments disclosed herein are for purposes of illustration and are not intended to be limiting, with the true scope and spirit being indicated by the following claims.

What is claimed is:

1. A non-transitory computer readable medium carrying computer executable instructions configured to cause a portable device to execute a method comprising the steps of:
   measuring a physical periodic motion of a peripheral artery with a pulse sensor,
   each measured physical periodic motion including a modulation and a pulse rate, wherein the modulation corresponds to a difference or ratio between systolic peak and diastolic hump corresponding to respective expansion of the peripheral artery during the physical periodic motion;
   receiving the modulation and the pulse rate with a microcontroller and saving the modulation and the pulse rate to a buffer memory as a modulation history and a pulse rate history,
   determining, with the microcontroller, at least one limit further including at least one of a modulation limit value, a pulse rate limit value, and a blood flow limit value, from the modulation history and the pulse rate history;
   writing the at least one limit to a non-transitory computer readable medium;
   comparing, with the microcontroller, one or more measured instances of the modulation, a blood flow rate, and the pulse rate to at least one of the modulation limit value, the pulse rate limit value, and the blood flow limit value; and
   outputting a prompt from the microcontroller via a user interface to a person if the one or more measured instances of the modulation, the blood flow rate, and the pulse rate falls outside the modulation limit value, the pulse rate limit value, and the blood flow limit value.

2. The non-transitory computer readable medium carrying computer executable instructions configured to cause a portable device to execute the method of claim 1, wherein comparing the one or more measured instances of the modulation, the blood flow rate, and the pulse rate to the modulation limit value, blood flow limit value, and pulse rate limit value further comprises:
   comparing at least three successive ones of the measured instances to a combined modulation and pulse rate limit; and
   wherein outputting a prompt from the microcontroller via a user interface to the person further comprises:
      outputting the prompt if and only if each of the at least three successive measured instances falls outside the modulation, blood flow and pulse rate limit.

3. The non-transitory computer readable medium carrying computer executable instructions configured to cause a portable device to execute the method of claim 1, wherein measuring a physical periodic motion of a peripheral artery with a pulse sensor further comprises:
   supporting one or more magnets on a flexible substrate adjacent to the person's skin such that the peripheral artery lies subjacent to the one or more magnets; and
   detecting a magnetic field variation produced by the one or more magnets responsive to physical pulsations received from the subjacent peripheral artery with a magnetic sensor.

4. The non-transitory computer readable medium carrying computer executable instructions configured to cause a portable device to execute the method of claim 1, wherein the step of determining further comprises:
   computing a standard deviation of a function of the instances, wherein the instances include modulation and blood flow rate divided by a corresponding pulse rate; and
   setting the limit as two standard deviations greater than a mean function value.

5. The non-transitory computer readable medium carrying computer executable instructions configured to cause a portable device to execute the method of claim 1, wherein the step of determining with the microcontroller further comprises:
   computing a slope of a function of the instances, the function including the modulation and the blood flow rate divided by a corresponding pulse rate; and
   setting the modulation limit value, the blood flow rate limit value, and the pulse rate limit value as a derivative of the slope times a constant greater than one.

6. The non-transitory computer readable medium carrying computer executable instructions configured to cause a portable device to execute the method of claim 1, wherein the prompt indicates that the person is dehydrated.

7. The non-transitory computer readable medium carrying computer executable instructions configured to cause a portable device to execute the method of claim 6, further comprising outputting the prompt if the pulse rate falls outside the pulse rate limit value and if the modulation falls outside the modulation limit value.

8. The non-transitory computer readable medium carrying computer executable instructions configured to cause a portable device to execute the method of claim 1, further comprising identifying the diastolic hump as a local maximum in expansion of the peripheral artery between a local minimum corresponding to a dicrotic notch and an overall minimum of a diameter of the peripheral artery as indicated by the pulse sensor.

9. The non-transitory computer readable medium carrying computer executable instructions configured to cause a portable device to execute the method of claim 8, wherein the systolic peak corresponds to an overall maximum expansion of the peripheral artery as indicated by the pulse sensor.

10. The non-transitory computer readable medium carrying computer executable instructions configured to cause a portable device to execute the method of claim 1, wherein the step of determining, with the microcontroller, the estimated blood flow rate further comprises
   determining, with the microcontroller, an estimated instantaneous blood flow rate.

* * * * *